United States Patent
Miyata et al.

(10) Patent No.: US 11,464,750 B2
(45) Date of Patent: Oct. 11, 2022

(54) ANTICANCER AGENT AND USE THEREOF

(71) Applicant: Shohei Miyata, Misato (JP)

(72) Inventors: Shohei Miyata, Misato (JP); Susumu Kitanaka, Narashino (JP); Liyan Wang, Shenzhen (CN); Tomonori Nakamura, Tokyo (JP)

(73) Assignee: Shohei Miyata, Misato (JP)

( * ) Notice: Subject to any disclaimer, the term of this patent is extended or adjusted under 35 U.S.C. 154(b) by 338 days.

(21) Appl. No.: 16/619,206

(22) PCT Filed: Jun. 12, 2018

(86) PCT No.: PCT/JP2018/022394
§ 371 (c)(1),
(2) Date: Mar. 5, 2020

(87) PCT Pub. No.: WO2018/230556
PCT Pub. Date: Dec. 20, 2018

(65) Prior Publication Data
US 2020/0253892 A1  Aug. 13, 2020

(30) Foreign Application Priority Data
Jun. 12, 2017  (JP) .............. JP2017-115388

(51) Int. Cl.
A61K 31/122  (2006.01)
A61P 35/00  (2006.01)
G01N 33/574  (2006.01)

(52) U.S. Cl.
CPC ............ A61K 31/122 (2013.01); A61P 35/00 (2018.01); G01N 33/574 (2013.01)

(58) Field of Classification Search
None
See application file for complete search history.

(56) References Cited

FOREIGN PATENT DOCUMENTS

| JP | 2004-531568 A | 10/2004 |
| JP | 2007-519752 A | 7/2007 |
| JP | 2009-013131 A | 1/2009 |
| JP | 2011-518114 A | 6/2011 |
| JP | 2012-500197 A | 1/2012 |
| JP | 2017-075113 A | 4/2017 |
| WO | 02/096408 A1 | 12/2002 |
| WO | 2005/074632 A2 | 8/2005 |
| WO | 2009/091550 A2 | 7/2009 |
| WO | 2010019271 A1 | 2/2010 |
| WO | 2011/083830 A1 | 7/2011 |

OTHER PUBLICATIONS

Liu et al., Tumor Biology (2016), 37(5), pp. 6227-6238.*
Fukuda, et al., "3EZ, 20Ac-Ingenol, a Catalytic Inhibitor of Topoisomerases, Downregulates p-Akt and Indues DSBs and Apoptosis of DT40 Cells," Arch. Pharm. Res. 36:1029-1038, 2013.
International Search Report dated Sep. 28, 2018, in corresponding PCT/JP2018/022394, filed Jun. 12, 2018, 4 pages.
Miyata, S., et al., "3EZ, 20Ac-Ingenol Induces Cell-Specific Apoptosis in Cyclin D1 Overexpression Through the Activation of ATR and Downregulation of p-Akt," Leukemia Research 64:46-51, 2018.
Miyata, S., et al., "Mechanism of the Inhibition of Leukemia Cell Growth and Induction of Apoptosis Through the Activation of ATR and PTEN by the Topoisomerase Inhibitor 3EZ, 20Ac-Ingenol," Leukemia Research 39:927-932, 2015.
Office Action dated May 31, 2022, issued in Chinese Application No. 201880038045.4, filed Jun. 12, 2018, 18 pages.
Sun, Dongdong, "The study of PTEN overexpression inhibiting canine mammary tumor cells growth by down-regulating PI3K/Akt pathway," Dissertation for the Master Degree, No. 3, pp. 2-3, Feb. 15, 2017.

* cited by examiner

Primary Examiner — Brian J Davis
(74) Attorney, Agent, or Firm — Christensen O'Connor Johnson Kindness PLLC

(57) ABSTRACT

An anticancer agent for cancers in which an abundance of cyclin D1 protein is greater than that in a control, the anticancer agent including a compound represented by the following Formula (1) as an active ingredient (in Formula (1), $R^1$ to $R^{11}$ each independently represent a hydrogen atom, an aliphatic group having 1 to 30 carbon atoms, or a group represented by Formula RCO— (where, R represents an aliphatic group having 1 to 30 carbon atoms, or an aromatic group or heteroaromatic group having 1 to 10 carbon atoms)).

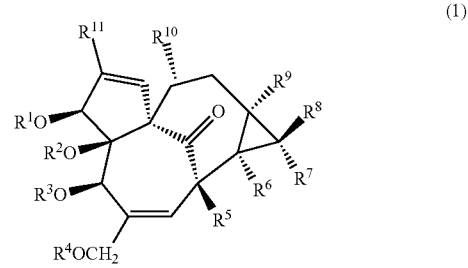

(1)

5 Claims, 19 Drawing Sheets

ANTICANCER AGENT AND USE THEREOF

TECHNICAL FIELD

The present invention relates to an anticancer agent and use thereof. More specifically, the present invention relates to an anticancer agent; a method for predicting whether administration of 3-O-(2'E,4'Z-decadienoyl)-20-O-acetylingenol (3EZ,20Ac-ingenol) or derivatives thereof is effective in treating a cancer; and a kit. Priority is claimed on Japanese Patent Application No. 2017-115388, filed Jun. 12, 2017, the content of which is incorporated herein by reference.

BACKGROUND ART

Topoisomerase is required for DNA synthesis and repair. Topoisomerase is an enzyme that eliminates kinking of DNA, cleaves a single strand or double strand of DNA, and eliminates kinking caused by DNA replication.

Topoisomerases are classified into topoisomerase I in which DNA cleavage is single-stranded, and topoisomerase II in which DNA cleavage is double-stranded.

A topoisomerase inhibitor is a compound that inhibits the activity of topoisomerase. Topoisomerase inhibitors are classified into a topoisomerase inhibitor of a DNA-cleavage type which inhibits activity of topoisomerase at the DNA cleavage stage; and a topoisomerase inhibitor of an enzyme-inhibiting type which inhibits activity of topoisomerase at stages other than the DNA cleavage stage.

Since cancer cells actively synthesize DNA, topoisomerase inhibitors are used as anticancer agents. The topoisomerase inhibitor of a DNA-cleavage type induces apoptosis of cancer cells by a DNA damage monitoring mechanism (DNA damage checkpoint). Meanwhile, the topoisomerase inhibitor of an enzyme-inhibiting type induces inhibition of cell division by a DNA kinking elimination monitoring mechanism (decatenation checkpoint). Currently, topoisomerase inhibitors used in anticancer agents are of a DNA-cleavage type.

3EZ,20Ac-ingenol is a kind of diterpenes that are extracted from *Euphorbia kansui*, which is a perennial plant of Euphorbiaceae. 3EZ,20Ac-ingenol is a topoisomerase inhibitor, and it is reported that it does not cause DNA cleavage and stops cell proliferation of DT40 cells, which are derived from chicken B cells, in the G2/M phase (for example, refer to Non-Patent Literature 1).

CITATION LIST

Non-Patent Literature

[Non-Patent Literature 1]
Yasuaki Fukuda, et al., 3EZ,20Ac-ingenol, a catalytic inhibitor of topoisomerases, downregulates p-Akt and induces DSBs and apoptosis of DT40 Arch. Pharm. Res., 36, 1029-1038, 2013.

SUMMARY OF INVENTION

Technical Problem

A mechanism of action of a topoisomerase inhibitor of a DNA-cleavage type as an anticancer agent is that it utilizes a monitoring mechanism induced by DNA damage, and this causes many side effects. For example, DNA cleavage that occurs due to treatment with the topoisomerase inhibitor of a DNA-cleavage type may cause secondary cancers after 2 to 3 years.

In addition, topoisomerase inhibitors tend to induce apoptosis in cells with rapid DNA synthesis. For this reason, in some cases, an amount of normal bone-marrow hematopoietic stem cells and undifferentiated cells which are rapidly proliferating is reduced, and thereby myelosuppression, leukopenia, or the like occur.

In addition, it is known that the heart has a high level of topoisomerase II activity. For this reason, when a topoisomerase inhibitor that inhibits topoisomerase II is administered, many cells undergo apoptosis in the heart, which may cause heart damage in some cases.

Meanwhile, because topoisomerase inhibitors of an enzyme-inhibiting type of the related art have a low level of cell proliferation inhibitory activity ($IC_{50}$=5 to 50 μM), multinucleated cells may be generated after a phase of a cell cycle having stopped, and these multinucleated cells may cause secondary cancers.

With such a background, an anticancer agent having fewer side effects such as occurrence of secondary cancers is desired. Accordingly, an object of the present invention is to provide an anticancer agent that specifically acts on a specific cancer without causing DNA cleavage.

Solution to Problem

The present invention includes the following aspects.

[1] An anticancer agent for cancers in which an abundance of cyclin D1 protein is greater than that in a control, the anticancer agent including a compound represented by the following Formula (1) (in Formula (1), $R^1$ to $R^{11}$ each independently represent a hydrogen atom, an aliphatic group having 1 to 30 carbon atoms, or a group represented by Formula RCO— (where, R represents an aliphatic group having 1 to 30 carbon atoms, or an aromatic group or heteroaromatic group having 1 to 10 carbon atoms)) as an active ingredient.

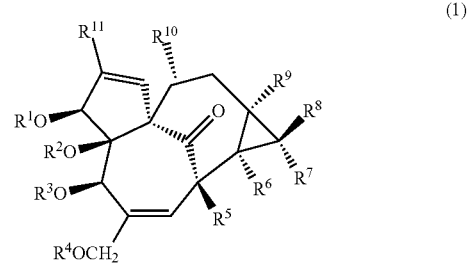

(1)

[2] A pharmaceutical composition for cancers in which an abundance of cyclin D1 protein is greater than that in a control, the pharmaceutical composition including the anticancer agent according to [1]; and a pharmaceutically acceptable carrier.

[3] A method for predicting whether administration of a compound represented by the above Formula (1) is effective in treating a cancer, the method including measuring an abundance of cyclin D1 protein in cells derived from the cancer, in which a result in which the measured abundance of cyclin D1 protein is greater than that in a control indicates that administration of the compound is effective in treating the cancer.

[4] A method for predicting whether administration of a compound represented by the above Formula (1) is effective in treating a cancer, the method including culturing cells derived from the cancer in the presence of the compound; and measuring transfer of cyclin D1 protein from a nucleus into a cytoplasm of the cell, in which the transfer of the cyclin D1 protein from the nucleus into the cytoplasm indicates that administration of the compound is effective in treating the cancer.

[5] A method for predicting whether administration of a compound represented by the above Formula (1) is effective in treating a cancer, the method including culturing cells derived from the cancer in the presence of the compound; and measuring an abundance of cyclin D1 protein in a nucleus of the cell, in which a decreased abundance of cyclin D1 protein in the nucleus indicates that administration of the compound is effective in treating the cancer.

[6] A method for predicting whether administration of a compound represented by the above Formula (1) is effective in treating a cancer, the method including culturing cells derived from the cancer in the presence of the compound; and measuring an abundance of phosphorylated Akt protein in a nucleus of the cell, in which a decreased abundance of phosphorylated Akt protein in the nucleus indicates that administration of the compound is effective in treating the cancer.

[7] A kit for predicting whether administration of a compound represented by the above Formula (1) is effective in treating a cancer, the kit including a specific binding substance for cyclin D1 protein.

[8] A kit for predicting whether administration of a compound represented by the above Formula (1) is effective in treating a cancer, the kit including a specific binding substance for phosphorylated Akt protein.

Advantageous Effects of Invention

According to the present invention, it is possible to provide an anticancer agent that specifically acts on a specific cancer without causing DNA cleavage.

DESCRIPTION OF EMBODIMENTS

[Anticancer Agent]

Figure 1:
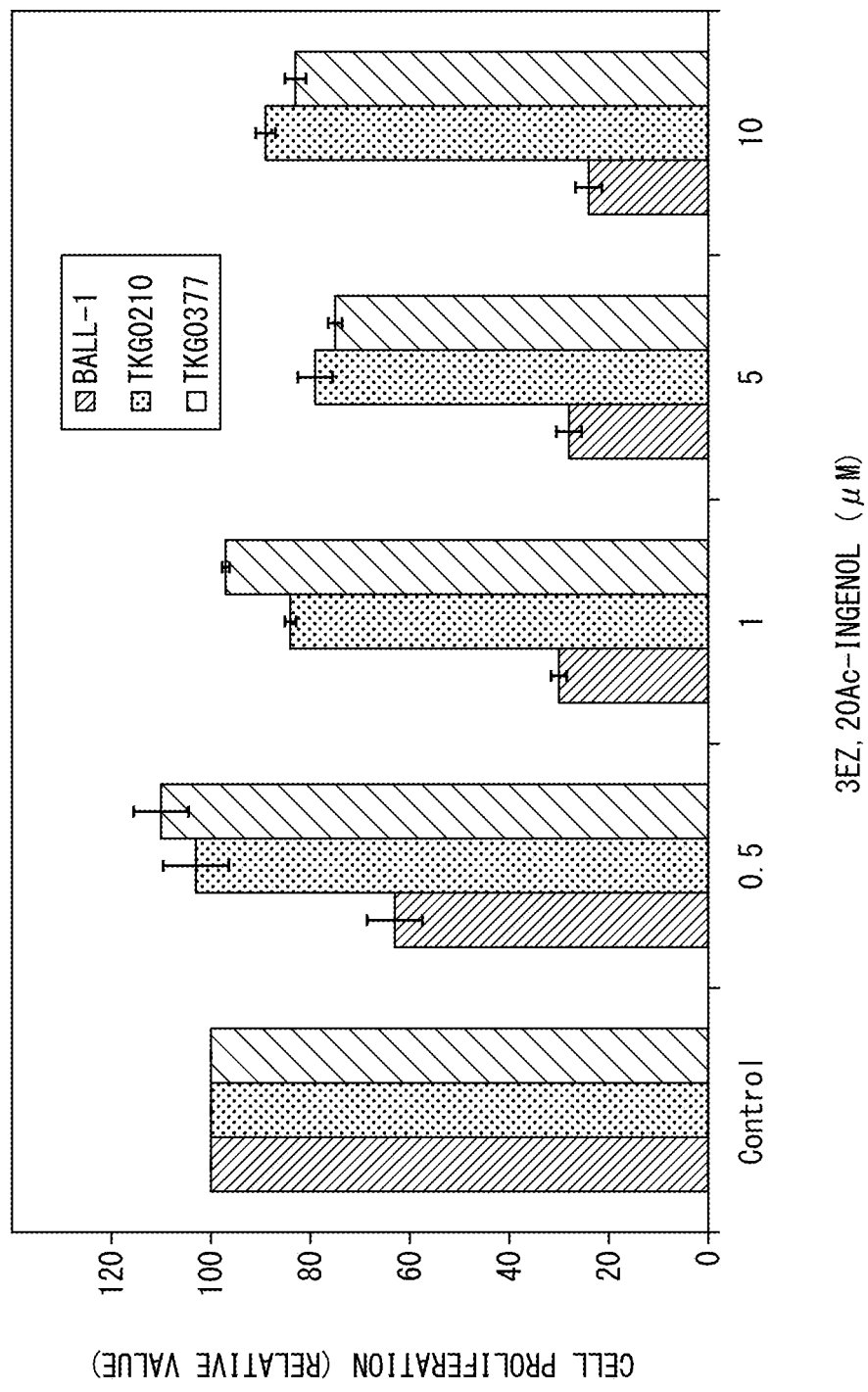
FIG. 1 is a graph showing results of MTT assay in Experimental Example 1.

In one embodiment, the present invention provides an anticancer agent for cancers in which an abundance of cyclin D1 protein is greater than that in a control, the anticancer agent including a compound represented by the following Formula (1) as an active ingredient. The anticancer agent of the present embodiment may be an agent for cancers in which an abundance of cyclin D1 protein in a nucleus is greater than that in the control.

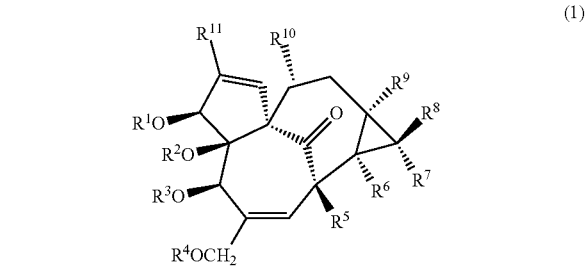

(1)

In Formula (1), $R^1$ to $R^{11}$ each independently represent a hydrogen atom, an aliphatic group having 1 to 30 carbon atoms, or a group represented by Formula RCO— (where, R represents an aliphatic group having 1 to 30 carbon atoms, or an aromatic group or heteroaromatic group having 1 to 10 carbon atoms).

In Formula (1), the aliphatic group is not particularly limited as long as effects of the anticancer agent of the present embodiment are exhibited, and it may be linear, branched, saturated, unsaturated, substituted, or unsubstituted. In addition, the number of carbon atoms of the aliphatic group may be, for example, 1 to 20, or may be, for example, 1 to 16. Examples of substituents of the aliphatic group include a halogen atom, a hydroxyl group, an ether group, a carbonyl group, a carboxyl group, an amino group, an amide group, and the like.

Among groups represented by Formula RCO— in Formula (1), examples of groups in which R is an aliphatic group include a group obtained by removing a hydroxyl group from a carboxyl group of a saturated fatty acid having 1 to 16 carbon atoms, such as acetic acid, propionic acid, butyric acid, 2,3-dimethylbutanoic acid, caprylic acid, capric acid, lauric acid, myristic acid, and palmitic acid; a group obtained by removing a hydroxyl group from a carboxyl group of an unsaturated fatty acid having 1 to 16 carbon atoms, such as 2,4-decadienoic acid; and the like.

In addition, in Formula (1), the aromatic group and the heteroaromatic group may be substituted or unsubstituted. Furthermore, the number of carbon atoms of the aromatic group and heteroaromatic group may be, for example, 1 to 8, or may be, for example, 1 to 6. Examples of substituents of the aromatic group and heteroaromatic group include a halogen atom, a hydroxyl group, an ether group, a carbonyl group, a carboxyl group, an amino group, an amide group, and the like.

In Formula (1), among the groups represented by Formula RCO—, examples of groups in which R is an aromatic group include a group obtained by removing a hydroxyl group from a carboxyl group of an aromatic carboxylic acid such as benzoic acid, phthalic acid, salicylic acid, and anthranilic acid; and the like.

In addition, in Formula (1), among the groups represented by Formula RCO—, examples of groups in which R is a heteroaromatic group include a group obtained by removing a hydroxyl group from a carboxyl group of a heteroaromatic carboxylic acid such as furan carboxylic acid, thiophene carboxylic acid, pyridine carboxylic acid, nicotinic acid, and isonicotinic acid; and the like.

In the compound represented by Formula (1), $R^2$, $R^3$, $R^5$, $R^6$, and $R^9$ may be hydrogen atoms, $R^7$, $R^8$, $R^{10}$, and $R^{11}$ may be methyl groups, $R^1$ may be a group represented by the following Formula (2) or (3) or a hydrogen atom, and $R^4$ may be an acetyl group. In the following Formulas (2) and (3), $R^{12}$ represents an alkyl group having 1 to 10 carbon atoms.

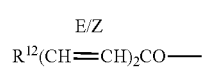

(2)

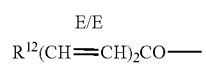

(3)

The compound represented by Formula (1) may be 3-O-(2'E,4'Z-decadienoyl)-20-O-acetylingenol (3EZ,20Ac-ingenol) represented by the following Formula (4), may be 3EE,20Ac-ingenol represented by the following Formula (5), or may be 20Ac-ingenol represented by the following Formula (6).

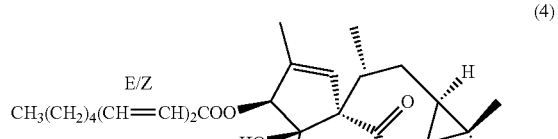

(4)

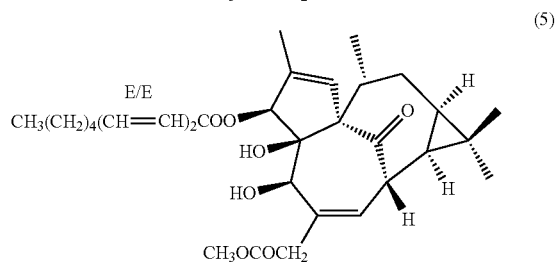

(5)

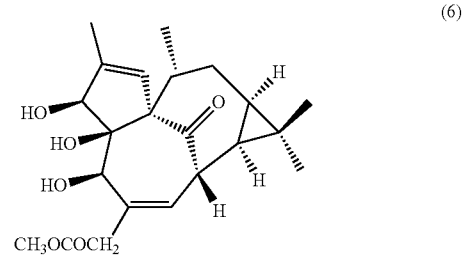

(6)

As will be described later in the Examples, the inventors of the present invention have made it clear that apoptosis is induced in a case where the compound represented by Formula (1) is administered to cancer cells in which an abundance of cyclin D1 protein is greater than that in a control. Accordingly, the anticancer agent of the present embodiment can be used for treating cancers in which an abundance of cyclin D1 protein is greater than that in a control.

As will be described later in the Examples, in a case where the compound represented by Formula (1) is administered to cancer cells in which an abundance of cyclin D1 protein is greater than that in a control, phosphorylation of H2AX is increased, and expression of p21 is also increased, which enhance DNA damage response. As a result, ATM/ATR is activated, p53 is phosphorylated and stabilized, and thereby apoptosis is induced. In addition, expression of PTEN is increased, p-Akt is inhibited, GSK-3β is activated, cyclin D1 is decomposed and proliferation thereof is inhibited, and thereby apoptosis is induced.

In the present specification, examples of cancers to be treated include human cancers and non-human animal cancers, and human cancers are preferable. In addition, a cancer may be a hematological cancer, a solid cancer, or the like.

In a case where an abundance of cyclin D1 protein is greater than that in a control, this means that an abundance of cyclin D1 protein in cells is greater than that in control cells. Examples of controls include a normal cell. The normal cell may be a normal blood cell, a cell derived from a normal tissue, or the like. The normal cell does not overexpress cyclin D1. That is, the compound represented by Formula (1) is an anticancer agent effective for cancer cells in which an abundance of cyclin D1 protein is greater than that in control cells. Alternatively, it can also be said that the compound represented by Formula (1) is an anticancer agent effective for cancer cells in which an abundance of cyclin D1 protein in a nucleus is greater than that in control cells. Alternatively, it can also be said that the compound represented by Formula (1) is an anticancer agent effective for cancer cells in which an expression level of cyclin D1 gene is higher than that in control cells.

As described in Non-Patent Literature 1, it became clear that the compound represented by Formula (1) does not cause DNA cleavage. Accordingly, the anticancer agent of the present embodiment does not cause DNA cleavage and thus is unlikely to cause secondary cancers even when it is used for a long time.

In addition, topoisomerase inhibitors of the related art tend to induce apoptosis in cells with rapid DNA synthesis, and when these inhibitors are administered to humans or non-human animals, in some cases, an amount of normal bone-marrow hematopoietic stem cells and undifferentiated cells which are rapidly proliferating is reduced, and thereby myelosuppression, leukopenia, or the like occur.

Meanwhile, the compound represented by Formula (1) is a topoisomerase inhibitor of an enzyme-inhibiting type, and is thought to induce a mechanism for monitoring DNA kinking elimination without causing DNA cleavage. In addition, it is known that the mechanism for monitoring DNA kinking elimination is deficient in stem cells, undifferentiated cells, and the like. Accordingly, even in a case where the anticancer agent of the present embodiment is administered to humans or non-human animals, it does not induce apoptosis of normal cells, stem cells and undifferentiated cells which do not overexpress cyclin D1 and in which the mechanism for monitoring DNA kinking elimination is deficient, and the like, and therefore myelosuppression and leukopenia are less likely to occur.

Furthermore, the compound represented by Formula (1) mainly targets topoisomerase I, not topoisomerase II having high activity in the heart. Accordingly, the anticancer agent of the present embodiment has few side effects on the heart in a case where it is administered to humans or non-human animals.

Based on the above descriptions, the anticancer agent of the present embodiment is useful as an anticancer agent having few side effects, because as long as normal cells, which rapidly proliferate, do not overexpress cyclin D1, apoptosis is not induced therein. Examples of cancers to be treated by the anticancer agent of the present embodiment include cancers in which an abundance of cyclin D1 protein is greater than that in a control. In addition, it is also useful for a case in which cyclin D1 is present in cytoplasmic fractions having granulosa cell components. Alternatively, it can be said that cancers to be treated by the anticancer agent of the present embodiment are cancers in which an expression level of cyclin D1 gene is higher than that of control cells.

In these cancers, there are various causes of increase in an abundance of cyclin D1 protein in cells over that in normal cells. For example, there is a case in which an abundance of cyclin D1 protein in a nucleus increases due to chromosomal translocation. In addition, there is a case in which cyclin D1 is overexpressed due to Wntβ catenin gene mutation, K-ras mutation, or catenin/APC gene mutation. The anticancer agent of the present embodiment can induce apoptosis in these cancers regardless of the cause of the increase in abundance of cyclin D1 protein in cells.

As the cause of overexpression of cyclin D1, there is a case in which, because PI3K/Akt is activated due to mutations in information transmission genes including cancer genes and cancer suppressor genes, decomposition of cyclin D1 (transfer of cyclin D1 into the cytoplasm) is inhibited, and therefore cyclin D1 is accumulated in the cells. Such a cancer is a cancer in which phosphorylation of an Akt protein is increased (a cancer in which a concentration of phosphorylated Akt protein in cells is increased), and the anticancer agent of the present embodiment is also effective for such a cancer.

The cancers to be treated by the anticancer agent of the present embodiment are more preferably cancers in which a phosphoinositide 3-kinase (PI3) kinase/Akt pathway is activated, and phosphorylation of Akt protein is increased (a concentration of phosphorylated Akt protein in cells is increased). As will be described later in the Examples, the anticancer agent of the present embodiment is particularly effective for cancers in which an abundance of cyclin D1 protein is greater than that in a control, and a concentration of phosphorylated Akt protein in cells is increased.

More specific examples of cancers to be treated by the anticancer agent of the present embodiment include mantle cell lymphoma, pancreatic cancer, brain tumors, pituitary tumors, esophageal cancer, breast cancer, and the like. In these cancers, an abundance of cyclin D1 protein may be greater than that in normal cells.

In these cancers, there are various causes of increase in an abundance of cyclin D1 protein over that in normal cells. For example, there is a case in which an abundance of cyclin D1 protein increases due to chromosomal translocation, and there is a case in which an abundance of cyclin D1 protein increases as a result of activation of a proliferation signal due to canceration. The anticancer agent of the present embodiment can induce apoptosis in these cancers regardless of the cause of the increase in abundance of cyclin D1 protein.

[Pharmaceutical Composition]

In one embodiment, the present invention provides a pharmaceutical composition for cancers in which an abundance of cyclin D1 protein is greater than that in a control, the pharmaceutical composition including the above-described anticancer agent; and a pharmaceutically acceptable carrier.

The pharmaceutical composition may be formulated into a dosage form used orally or a dosage form used parenterally. Examples of dosage forms used orally include tablets, capsules, elixirs, microcapsules, and the like. Examples of dosage forms used parenterally include injections, suppositories, patches, and the like.

As the pharmaceutically acceptable carrier, carriers generally used for formulation of pharmaceutical compositions can be used without particular limitation. More specific examples thereof include binders such as gelatin, corn starch, gum tragacanth, and gum arabic; excipients such as starch and crystalline cellulose; swelling agents such as alginic acid; injectable solvents such as water, ethanol, and glycerin; adhesives such as rubber adhesives and silicone adhesives; and the like.

The pharmaceutical composition may include an additive. Examples of additives include lubricants such as magnesium stearate; sweeteners such as sucrose, lactose, and saccharin; flavoring agents such as peppermint and a *Gaultheria adenothrix* oil; stabilizers such as benzyl alcohol and phenol; buffering agents such as phosphates and sodium acetate; solubilizing agents such as benzyl benzoate and benzyl alcohol; antioxidants; preservatives; surfactants; emulsifiers; and the like.

The pharmaceutical composition can be formulated by appropriately combining the above-mentioned carriers and additives, and mixing them in a unit dosage form required for generally recognized pharmaceutical practice.

Administration to a patient may be performed by, for example, intraarterial injection, intravenous injection, subcutaneous injection, and the like, and may be performed intranasally, transbronchially, intramuscularly, transdermally, or orally by methods known to those skilled in the art. A dosage varies depending on a weight and age of a patient, administration methods, and the like, and those skilled in the art can appropriately select an appropriate dosage.

A dosage of the compound varies depending on symptoms. In a case of oral administration, it is generally about 0.1 to 100 mg, preferably about 1.0 to 50 mg, and more preferably about 1.0 to 20 mg per day for an adult (with a body weight of 60 kg).

In a case of parenteral administration, a single dosage varies depending on administration targets, target organs, symptoms, and administration methods. For example, in the form of an injection, in general, it is advantageous to administer about 0.01 to 30 mg, preferably about 0.1 to 20 mg, and more preferably about 0.1 to 10 mg per day by intravenous injection for an adult (with a body weight of 60 kg).

[Method for Predicting Whether Administration of Compound Represented by Formula (1) is Effective in Treating Cancer]

First Embodiment

In one embodiment, the present invention provides a method for predicting whether administration of a compound represented by Formula (1) is effective in treating a cancer, the method including measuring an abundance of cyclin D1 protein in cells derived from the cancer, in which a result in which the measured abundance of cyclin D1 protein is greater than that in a control indicates that administration of the compound is effective in treating the cancer.

In the method of the present embodiment, a method of measuring an abundance of cyclin D1 protein is not particularly limited, and for example, it can be measured by RT-PCR, Western blotting, immunohistochemical staining, or the like. As will be described later, cyclin D1 in cytoplasm is rapidly decomposed by proteasomes. Accordingly, it can be said that cells with a high expression level of cyclin D1 gene have a high abundance of cyclin D1 protein in a nucleus.

In addition, in the method of the present embodiment, a control is the same as that mentioned above, and examples thereof include normal cells and the like.

Furthermore, as cells derived from a cancer to be treated, it is possible to use, for example, blood cells derived from biopsy samples, cells derived from cancer tissue excised by surgery, and the like.

According to the method of the present embodiment, in a case where an abundance of cyclin D1 protein in cells derived from a cancer to be treated is greater than that in a control, it can be determined that administration of the compound represented by Formula (1) is effective in treatment.

Second Embodiment

In one embodiment, the present invention provides a method for predicting whether administration of a compound represented by Formula (1) is effective in treating a cancer, the method including culturing cells derived from the cancer in the presence of the compound; and measuring transfer of cyclin D1 protein from a nucleus into a cytoplasm of the cell, in which the transfer of the cyclin D1 protein from the nucleus into the cytoplasm indicates that administration of the compound is effective in treating the cancer.

As will be described later in the Examples, in cancer cells in which inhibition of cell proliferation and induction of apoptosis, which have occurred due to administration of the compound represented by Formula (1), are recognized, it was observed that cyclin D1 present in the nucleus transferred into the cytoplasm due to the administration of the compound represented by Formula (1).

Accordingly, as a result of culturing cells derived from a cancer to be treated in the presence of the compound represented by Formula (1), in a case where cyclin D1 transfers from the nucleus to the cytoplasm, it can be determined that administration of the compound represented by formula (1) is effective in treating the cancer.

In the method of the second embodiment, a concentration of the compound represented by Formula (1) added to a cell medium may be about 0.5 to 10 µM at a final concentration. In addition, the transfer of cyclin D1 from the nucleus into the cytoplasm of a cell can be confirmed, for example, within about 24 to 48 hours after administration of the compound represented by Formula (1).

Furthermore, the transfer of cyclin D1 from the nucleus to the cytoplasm can be confirmed by fractionating cells into a nuclear fraction and a cytoplasm fraction; performing Western blotting using an anti-cyclin D1 antibody; and the like. Alternatively, localization of cyclin D1 in cells may be confirmed by fixing the cells and immunostaining them with an anti-cyclin D1 antibody.

<<Modification Example of Second Embodiment>>

In the method of the second embodiment, in a case where cyclin D1 transfers from the nucleus into the cytoplasm of a cell, an abundance of cyclin D1 in the nucleus decreases. Accordingly, using the decrease in abundance of cyclin D1 in the nucleus as an indicator, it is also possible to predict whether or not administration of the compound represented by Formula (1) is effective in treating a cancer.

In addition, in a case where cyclin D1 transfers from the nucleus into the cytoplasm of a cell, an abundance of cyclin D1 in the cytoplasm increases. Accordingly, using the increase in abundance of cyclin D1 in the cytoplasm as an indicator, it is also possible to predict whether or not administration of the compound represented by Formula (1) is effective in treating a cancer. However, since cyclin D1 in the cytoplasm is decomposed by proteasomes, the increase in an abundance of cyclin D1 in the cytoplasm is temporary.

That is, the cyclin D1 protein transfers from the nucleus into the cytoplasm and is further decomposed in the cytoplasm. Accordingly, using the temporary increase and further decrease in abundance of cyclin D1 in the cytoplasm as an indicator, it is also possible to predict whether or not administration of the compound represented by Formula (1) is effective in treating a cancer.

Third Embodiment

In one embodiment, the present invention provides a method for predicting whether administration of a compound represented by Formula (1) is effective in treating a cancer, the method including culturing cells derived from the cancer in the presence of the compound; and measuring an abundance of phosphorylated Akt protein in a cytoplasm or nucleus of the cell, in which a decreased abundance of phosphorylated Akt protein in the cytoplasm or nucleus indicates that administration of the compound is effective in treating the cancer.

The phosphorylated Akt protein is an activated Akt protein. Examples of phosphorylated Akt proteins include an Akt protein in which the 473th serine residue of the Akt protein is phosphorylated. The phosphorylated Akt protein present in the cytoplasm or nucleus controls a decomposition reaction of cyclin D1.

As will be described later in the Examples, in cancer cells in which inhibition of cell proliferation and induction of apoptosis, which have occurred due to administration of the compound represented by Formula (1), are recognized, an abundance of phosphorylated Akt protein in the cytoplasm or nucleus significantly decreased due to the administration of the compound represented by Formula (1).

Accordingly, as a result of culturing cells derived from a cancer to be treated in the presence of the compound represented by Formula (1), in a case where an abundance of phosphorylated Akt protein in the cytoplasm or nucleus decreases, it can be determined that administration of the compound represented by formula (1) is effective in treating the cancer.

In the method of the third embodiment, a concentration of the compound represented by Formula (1) added to a cell medium may be about 0.5 to 10 μM at a final concentration. In addition, the decrease in abundance of phosphorylated Akt protein in the cytoplasm or nucleus can be confirmed, for example, within about 24 to 48 hours after administration of the compound represented by Formula (1).

Furthermore, the decrease in abundance of phosphorylated Akt protein in the cytoplasm or nucleus can be confirmed by fractionating cells into a nuclear fraction and a cytoplasm fraction; performing Western blotting using an anti-p-Akt (Ser$^{473}$) antibody; and the like. Alternatively, an abundance of phosphorylated. Akt protein in the cytoplasm or nucleus can be confirmed by fixing the cells and immunostaining them with an anti-p-Akt (Ser$^{473}$) antibody.

[Kit]

First Embodiment

In one embodiment, the present invention provides a kit for predicting whether administration of a compound represented by Formula (1) is effective in treating a cancer, the kit including a specific binding substance for cyclin D1 protein.

With the kit of the present embodiment, it is possible to perform the above-described method of the second embodiment which is for predicting whether administration of the compound represented by Formula (1) is effective in treating a cancer.

The cyclin D1 protein is preferably cyclin D1 of an animal species to be treated. In a case where a cancer to be treated is a human cancer, the cyclin D1 protein is preferably a human cyclin D1 protein.

Examples of specific binding substances include antibodies, antibody fragments, aptamers, and the like. An antibody can be produced by, for example, immunizing an animal such as a mouse with a target substance or a fragment thereof as an antigen. Alternatively, for example, an antibody can be produced by screening a phage library. Examples of antibody fragments include Fv, Fab, scFv, and the like. An antibody may be a monoclonal antibody or a polyclonal antibody. In addition, a commercially available antibody may also be used.

An aptamer is a substance having a specific binding ability with respect to a target substance. Examples of aptamers include nucleic acid aptamers, peptide aptamers, and the like. Nucleic acid aptamers having a specific binding ability with respect to a target substance can be selected by, for example, a systematic evolution of ligand by exponential enrichment (SELEX) method, or the like. Peptide aptamers having a specific binding ability with respect to a target substance can be selected by, for example, a two-hybrid method using yeast, or the like.

The kit of the present embodiment may further include the compound represented by Formula (1). In addition, the kit of the present embodiment may further include a specific binding substance for phosphorylated Akt protein, which will be described later.

Second Embodiment

In one embodiment, the present invention provides a kit for predicting whether administration of a compound represented by Formula (1) is effective in treating a cancer, the kit including a specific binding substance for phosphorylated Akt protein.

With the kit of the present embodiment, it is possible to perform the above-described method of the third embodiment which is for predicting whether administration of the compound represented by Formula (1) is effective in treating a cancer. The phosphorylated Akt protein is an activated Akt protein. Examples of phosphorylated Akt proteins include an Akt protein in which the 473th serine residue of the Akt protein is phosphorylated.

The phosphorylated Akt protein is preferably a phosphorylated Akt protein of an animal species to be treated. In a case where a cancer to be treated is a human cancer, the phosphorylated Akt protein is preferably a human phosphorylated Akt protein.

In the kit of the second embodiment, a specific binding substance is the same as that described above, and examples thereof include antibodies, antibody fragments, aptamers, and the like. In addition, the kit of the second embodiment may further include the compound represented by Formula (1). Furthermore, the kit of the second embodiment may further include a specific binding substance for the above-described cyclin D1 protein.

Other Embodiments

In one embodiment, the present invention provides a method for treating cancers, including measuring an abundance of cyclin D1 protein in cancer cells derived from a cancer patient, and administering an effective amount of a compound represented by the following Formula (1) to the cancer patient in a case where the measured abundance of cyclin D1 protein is greater than that in a control.

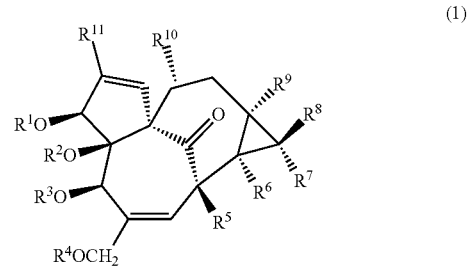

(1)

In Formula (1), $R^1$ to $R^{11}$ each independently represent a hydrogen atom, an aliphatic group having 1 to 30 carbon atoms, or a group represented by Formula RCO— (where, R represents an aliphatic group having 1 to 30 carbon atoms, or an aromatic group or heteroaromatic group having 1 to 10 carbon atoms).

In one embodiment, the present invention provides a method for treating cancers, including culturing cancer cells derived from a cancer patient in the presence of the compound represented by Formula (1), measuring transfer of cyclin D1 protein from a nucleus into a cytoplasm of the cell, and administering an effective amount of the compound represented by Formula (1) to the cancer patient in a case where the cyclin D1 protein transferred from the nucleus into the cytoplasm.

In one embodiment, the present invention provides a method for treating cancers, including culturing cancer cells derived from a cancer patient in the presence of the compound represented by Formula (1), measuring an abundance of cyclin D1 protein in a nucleus of the cell, and administering an effective amount of the compound represented by Formula (1) to the cancer patient in a case where the abundance of cyclin D1 protein in the nucleus decreased.

In one embodiment, the present invention provides a method for treating cancers, including culturing cancer cells derived from a cancer patient in the presence of the compound represented by Formula (1), measuring an abundance of phosphorylated Akt protein in a cytoplasm or nucleus of the cell, and administering an effective amount of the compound represented by Formula (1) to the cancer patient in a case where the abundance of phosphorylated Akt protein in the cytoplasm or nucleus decreased.

In the treatment methods of the respective embodiments, a concentration of the compound represented by Formula (1) added to a cell medium may be about 0.5 to 10 µM at a final concentration. In addition, the transfer of cyclin D1 from the nucleus into the cytoplasm of the cell, the decrease in abundance of cyclin D1 protein in the nucleus, and the decrease in abundance of phosphorylated Akt protein in the nucleus can be confirmed, for example, within about 24 to 48 hours after starting cell culture in the presence of the compound represented by Formula (1). In addition, a control is the same as that mentioned above, and examples thereof include normal cells and the like.

In one embodiment, the present invention provides a method for treating cancers in which an abundance of cyclin D1 protein is greater than that in a control, the method including administering an effective amount of the compound represented by Formula (1) to a patient in need of treatment.

In one embodiment, the present invention provides a method for treating cancers in which an expression level of cyclin D1 gene is higher than that of a control, the method including administering an effective amount of the compound represented by Formula (1) to a patient in need of treatment.

In one embodiment, the present invention provides a compound represented by Formula (1) for treating cancers in which an abundance of cyclin D1 protein is greater than that in a control.

In one embodiment, the present invention provides a compound represented by Formula (1) for treating cancers in which an expression level of cyclin D1 gene is higher than that of a control.

In one embodiment, the present invention provides use of a compound represented by Formula (1) for producing a therapeutic agent for cancers in which an abundance of cyclin D1 protein is greater than that in a control.

In one embodiment, the present invention provides use of a compound represented by Formula (1) for producing a therapeutic agent for cancers in which an expression level of cyclin D1 gene is higher than that of a control.

In each of these embodiments, the compound represented by Formula (1) may be in the form of a composition containing a pharmaceutically acceptable carrier. Examples of pharmaceutically acceptable carriers include carriers described above.

In addition, in each of these embodiments, a control is the same as that mentioned above, and examples thereof include normal cells and the like.

EXAMPLES

Next, the present invention will be described in more detail by showing experimental examples, but the present invention is not limited to the following experimental examples.

Experimental Example 1

(3EZ,20Ac-Ingenol Treatment Inhibited Proliferation of BALL-1 Cells)

BALL-1 cells of a cell line derived from a human mantle cell lymphoma, TKG0210 cells of a human myeloid leukemia cell line, and TKG0377 cells of a human T cell acute leukemia cell line were seeded in 96-well plates at $2.5 \times 10^4$ cells/well/100 µL, and cultured for 48 hours in the presence of 3EZ,20Ac-ingenol at final concentrations of 0 (control), 0.5, 1, 5, and 10 µM. Subsequently, cell proliferation was examined by MTT assay using a Cell Proliferation Kit 1 (Roche Applied Science).

FIG. 1 is a graph showing results of MTT assay. As a result, it became clear that 3EZ,20Ac-ingenol reduced a survival rate of each cancer cell line in a concentration-dependent manner within a range of 0 to 10 µM.

In particular, it became clear that 70% to 75% of the BALL-1 cells were killed after culturing them for 48 hours in the presence of 1 to 10 µM of 3EZ,20Ac-ingenol. In addition, it became clear that 5% to 20% of the TKG0210 cells and TKG0377 cells were killed after culturing them for 48 hours in the presence of 1 to 10 µM of 3EZ,20Ac-ingenol.

Experimental Example 2

(3EZ,20Ac-Ingenol Treatment Inhibited Proliferation of JeKo-1 Cells and Panc-1 Cells)

JeKo-1 cells of a cell line derived from a human mantle cell lymphoma were seeded in a 96-well plate at $1 \times 10^4$ cells/well/100 µL. In addition, Panc-1 cells of a cell line derived from a human pancreatic cancer were seeded in a 96-well plate at $3 \times 10^3$ cells/well/100 µL.

Subsequently, 3EZ,20Ac-ingenol at final concentrations of 0 (control), 0.1, 0.5, 1, 5, and 10 µM was added the wells of the respective cells, and culturing was performed for 48 hours. Subsequently, cell proliferation was examined by MTT assay using a Cell Proliferation Kit I (Roche Applied Science).

Figure 2:
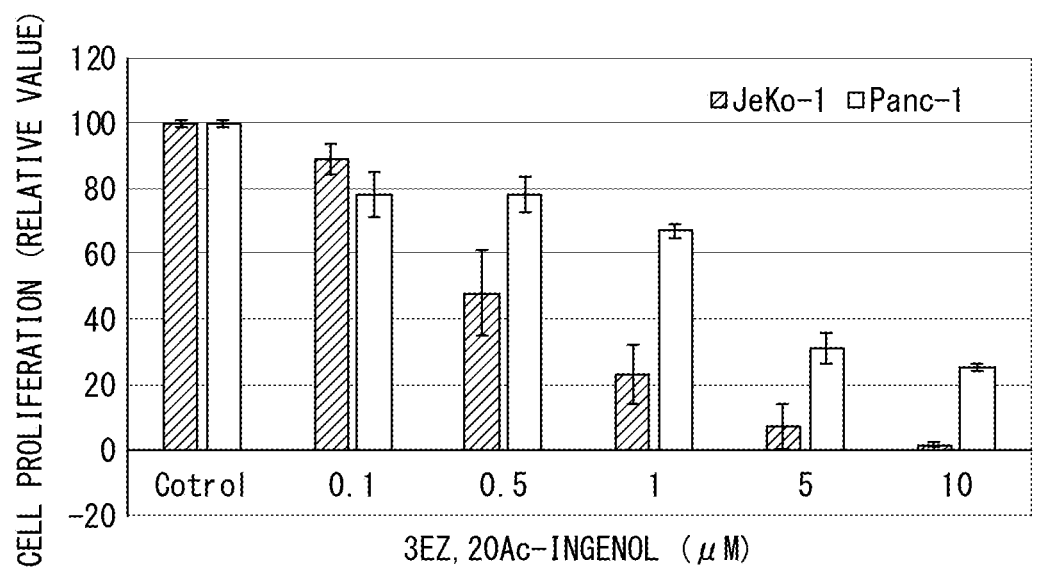
FIG. 2 is a graph showing results of MTT assay in Experimental Example 2.
Figure 3:
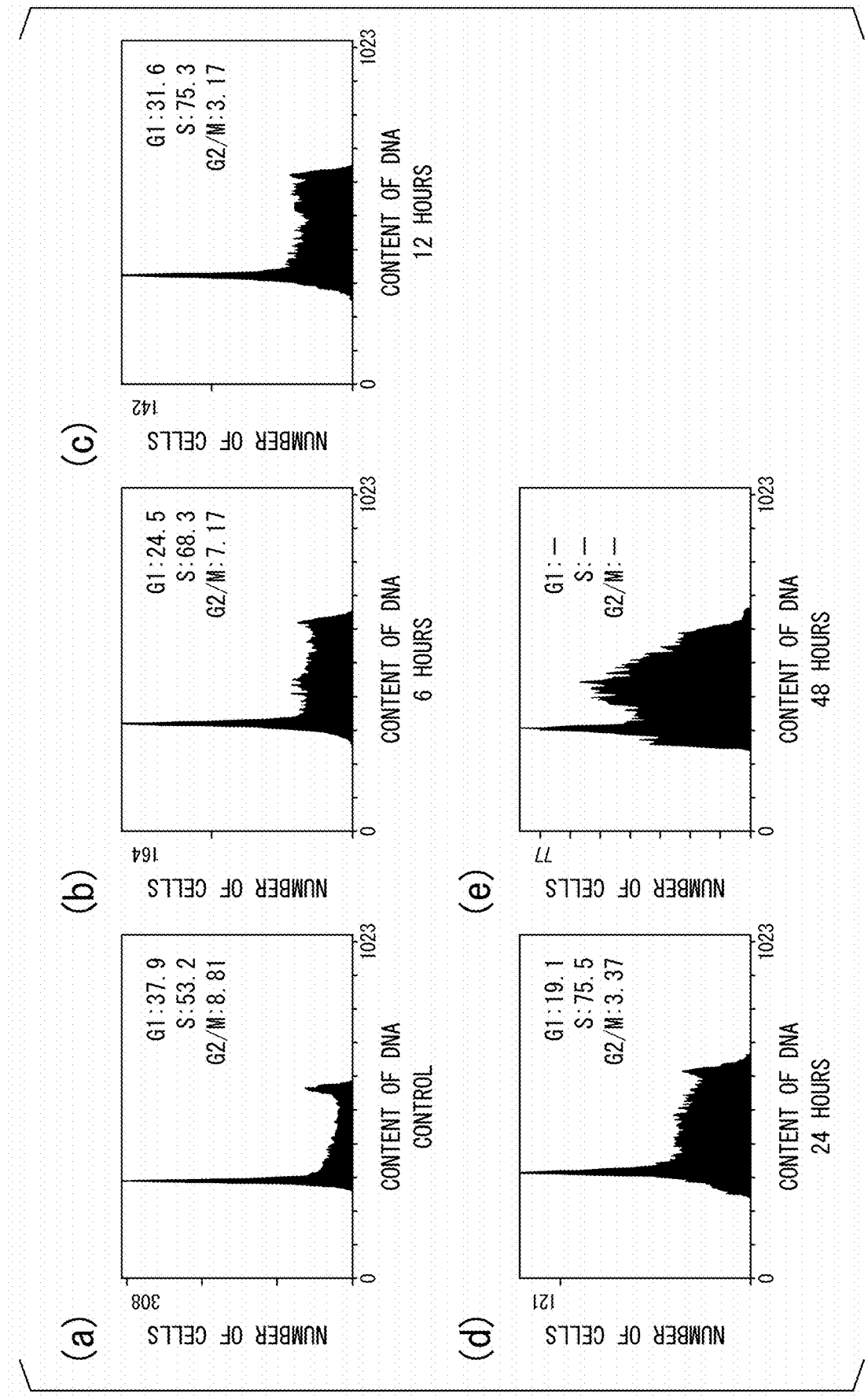
FIGS. 3(a) to 3(e) are graphs showing results of flow cytometry in Experimental Example 3.

FIG. 2 is a graph showing results of MIT assay. As a result, it became clear that 3EZ,20Ac-ingenol inhibited the proliferation of the JeKo-1 cells and Panc-1 cells in a concentration-dependent manner within a range of 0 to 10 µM.

More specifically, when the JeKo-1 cells were cultured for 48 hours in the presence of 1 to 10 μM of 3EZ,20Ac-ingenol, proliferation inhibition was recognized to the extent that grown cells were almost eliminated. In addition, when the Panc-1 cells were cultured for 48 hours in the presence of 1 to 10 μM of 3EZ,20Ac-ingenol, proliferation inhibition was recognized to the extent that only 20% to 30% of the cells survived.

Experimental Example 3

(3EZ,20Ac-Ingenol Treatment Stopped Cell Proliferation in S Phase)

Whether the inhibition of proliferation of the cancer cells by 3EZ,20Ac-ingenol was due a phase in which a cell cycle was stopped was examined.

Specifically, BALL-1 cells were treated with 3EZ,20Ac-ingenol at a final concentration of 0.5 μM for 6, 12, 24, and 48 hours, and then a phase of a cell cycle was analyzed using flow cytometry. In addition, cells that were not treated with 3EZ,20Ac-ingenol were used as controls.

FIGS. 3(a) to 3(e) are graphs showing results of flow cytometry analysis. In the present analysis, living cells were gated. As a result, it became clear that 3EZ,20Ac-ingenol treatment increased a proportion of S-phase cells to 68% after 6 hours, and to 75% after 12 hours and 24 hours. Meanwhile, in the control cells, a proportion of S-phase cells remained at 53%.

In addition, it became clear that 3EZ,20Ac-ingenol treatment decreased a proportion of G2/M-phase cells to about 3% after 12 hours and 24 hours. Meanwhile, in the control cells, a proportion of G2/M-phase cells was about 9%.

Similarly, it became clear that 3EZ,20Ac-ingenol treatment decreased a proportion of G1-phase cells to about 19% after 24 hours. Meanwhile, in the control cells, a proportion of G1-phase cells was about 38%. In addition, a proportion of cells in each phase of a cell cycle after 48 hours could not be calculated.

The above results indicate that cell proliferation of the BALL-1 cells was stopped in the S phase by being treated with 3EZ,20Ac-ingenol.

Experimental Example 4

(3EZ,20Ac-Ingenol Treatment Induced Apoptosis of BALL-1 Cells)

The induction of apoptosis by 3EZ,20Ac-ingenol treatment was examined by detecting histone-binding DNA fragmentation in the cytoplasm using a Cell Death Detection ELISA kit (Roche Applied Science).

Specifically, BALL-1 cells, TKG0210 cells, and TKG0377 cells were inserted into tubes at $5 \times 10^4$ cells/well/200 μL, and incubated for 6, 12, 24, 48, and 72 hours in the presence of 3EZ,20Ac-ingenol at a final concentration of 0.5 μM. Subsequently, the respective cells were lysed in a lysis buffer. Subsequently, the supernatant of cell debris of the respective cells was collected and transferred to an ELISA plate, and an absorbance at a wavelength of 405 nm was measured to measure the induction of apoptosis.

Figure 4:
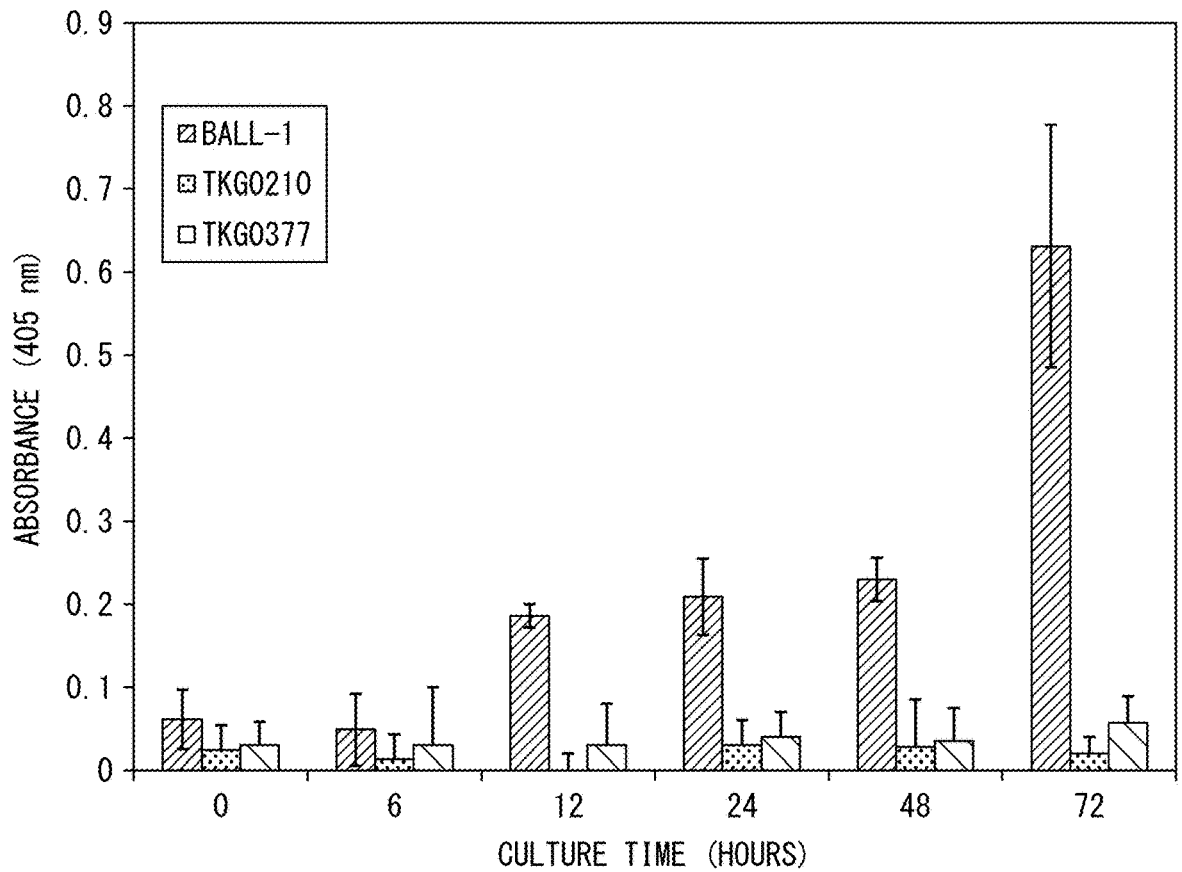
FIG. 4 is a graph showing results of measuring inducing of apoptosis in Experimental Example 4.

FIG. 4 is a graph showing results of measuring induction of apoptosis. As a result, it became clear that incubation of the BALL-1 cells for 72 hours in the presence of 3EZ,20Ac-ingenol at a final concentration of 0.5 μM noticeably increased the amount of fragmented DNA. On the other hand, although the TKG0210 cells and TKG0377 cells were incubated for 72 hours in the presence of 3EZ,20Ac-ingenol at a final concentration of 0.5 μM, almost no fragmented DNA was detected.

The above results indicate that apoptosis of BALL-1 cells was induced by 3EZ,20Ac-ingenol treatment.

Experimental Example 5

(3EZ,20Ac-Ingenol Treatment Induced Apoptosis of Panc-1 Cells)

The induction of apoptosis by 3EZ,20Ac-ingenol treatment was examined by detecting histone-binding DNA fragmentation in the cytoplasm using a Cell Death Detection RASA kit (Roche Applied Science).

Specifically, Panc-1 cells were inserted into tubes at $5 \times 10^3$ cells/well/100 μL, and incubated for 6, 12, 24, 48, and 72 hours in the presence of 3EZ,20Ac-ingenol at a final concentration of 3 μM. Subsequently, the respective cells were lysed in a lysis buffer. Subsequently, the supernatant of cell debris of the respective cells was collected and transferred to an ELISA plate, and an absorbance at a wavelength of 405 nm was measured to measure the induction of apoptosis.

Figure 5:
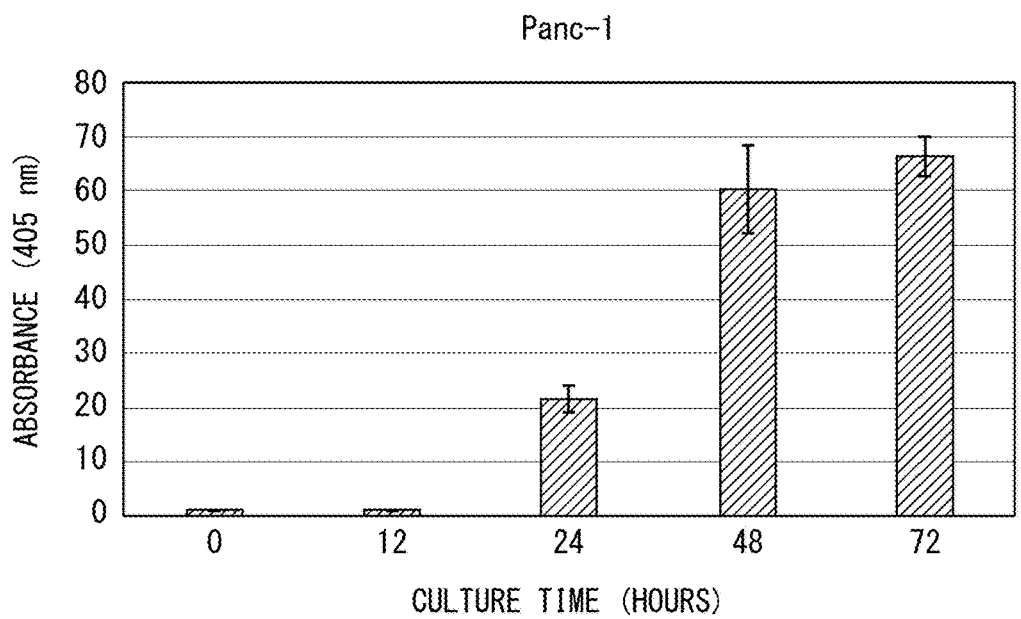
FIG. 5 is a graph showing results of measuring inducing of apoptosis in Experimental Example 5.

FIG. 5 is a graph showing results of measuring induction of apoptosis. As a result, it became clear that when the Panc-1 cells were incubated in the presence of 3EZ,20Ac-ingenol at a final concentration of 3 μM, DNA fragmentation started 24 hours after the incubation, and the amount of fragmented DNA further increased 48 hours and 72 hours thereafter.

The above results indicate that apoptosis of Panc-1 cells was induced by 3EZ,20Ac-ingenol treatment.

Experimental Example 6

(Induction of Apoptosis by 3EZ,20Ac-Ingenol Treatment is Associated with Activation of Caspase 3)

The induction of apoptosis in JeKo-1 cells and Panc-1 cells by 3EZ,20Ac-ingenol treatment was confirmed by detecting an activation reaction of a caspase 3.

Specifically, JeKo-1 cells were cultured for 0 (control), 12, 24, and 48 hours in the presence of 0.5 μM of 3EZ,20Ac-ingenol. In addition. Panc-1 cells were cultured for 0 (control), 12, 24, and 48 hours in the presence of 3 μM of 3EZ,20Ac-ingenol. Subsequently, activation of caspase 3 in the respective cells was detected by Western blotting using an anti-activated-caspase antibody (R & D Systems). Furthermore, as a loading control, actin protein was detected using an anti-actin antibody (Sigma).

Figure 6:
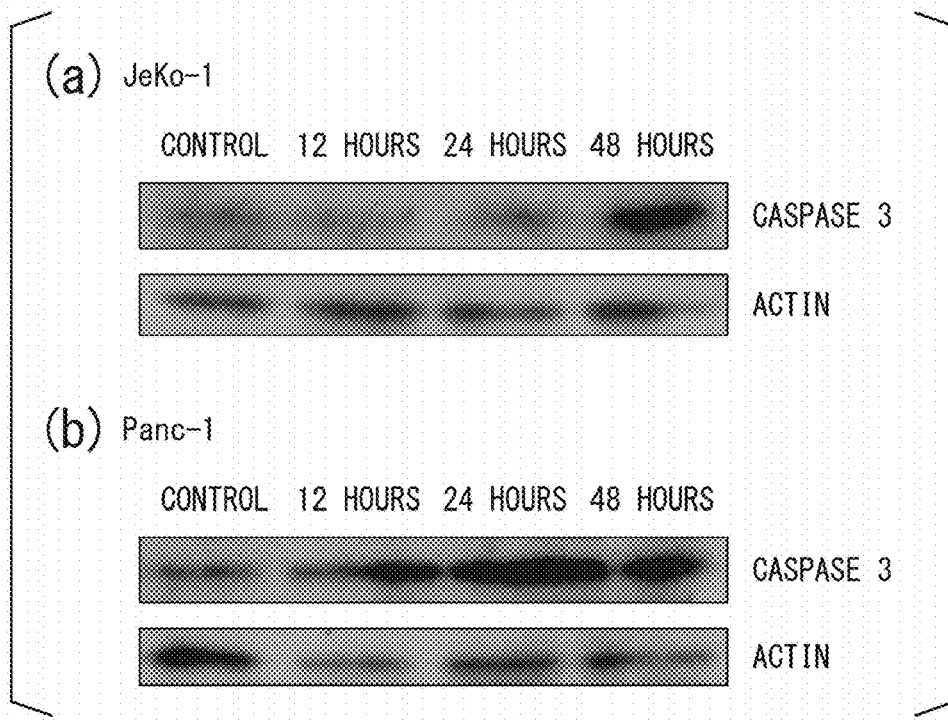
FIGS. 6(a) and 6(b) are photographs showing results of Western blotting in Experimental Example 6.

FIGS. 6(a) and 6(b) are photographs showing results of Western blotting. FIG. 6(a) shows results of JeKo-1 cells, and FIG. 6(b) shows results of Panc-1 cells. As a result, in the JeKo-1 cells, activation of caspase 3 was observed 48 hours after 3EZ,20Ac-ingenol treatment. Meanwhile, in the Panc-1 cells, activation of caspase 3 was observed 12 hours after 3EZ,20Ac-ingenol treatment.

Experimental Example 7

(Examination of phosphorylation of H2AX and expression of p21 protein by 3EZ,20Ac-Ingenol Treatment)

It is well known that administration of a topoisomerase inhibitor of a DNA-cleavage type induces a DNA damage response in cells and causes phosphorylation of H2AX. In addition, in cells having a large abundance of cyclin D1 protein, increase of H2AX phosphorylation, increase of expression of p21 protein, and activation of caspase 3 are recognized in a case where DNA damage occurs, and because of this property, also in BALL-1 cells, Jeko-1 cells, and Panc-1 cells having a large abundance of cyclin D1 protein in the cells, apoptosis may be induced from specific proliferation inhibition by 3EZ,20Ac-ingenol treatment.

The inventors of the present invention have clarified that 3EZ,20Ac-ingenol treatment induces inhibition of S-phase synthesis by inhibition of single-stranded DNA synthesis, as in a topoisomerase inhibitor of a DNA-cleavage type. From these findings, the inventors of the present invention have presumed that, in cells having a large abundance of cyclin D1, an abundance of phosphorylated H2AX (γH2AX), which is a DNA cleavage marker, is increased by treatment with 3EZ,20Ac-ingenol that does not cause DNA cleavage, this increase induces the same response as DNA damage response, and therefore apoptosis is induced from proliferation inhibition.

Accordingly, changes in phosphorylation of H2AX and an expression level of p21 protein by treating JeKo-1 cells and Panc-1 cells with 3EZ,20Ac-ingenol were examined by Western blotting.

Specifically, JeKo-1 cells were cultured for 0 (control), 12, 24 and 48 hours in the presence of 0.5 μM of 3EZ,20Ac-ingenol. In addition, Panc-1 cells were cultured for 0 (control), 12, 24, and 48 hours in the presence of 3 μM of 3EZ,20Ac-ingenol.

Subsequently, phosphorylation of H2AX in the respective cells was detected using an anti-phosphorylated-H2AX antibody (Millipore). In addition, p21 protein was detected using an anti-p21 antibody (Cell Signaling Technology). Furthermore, as a loading control, actin protein was detected using an anti-actin antibody (Sigma).

Figure 7:
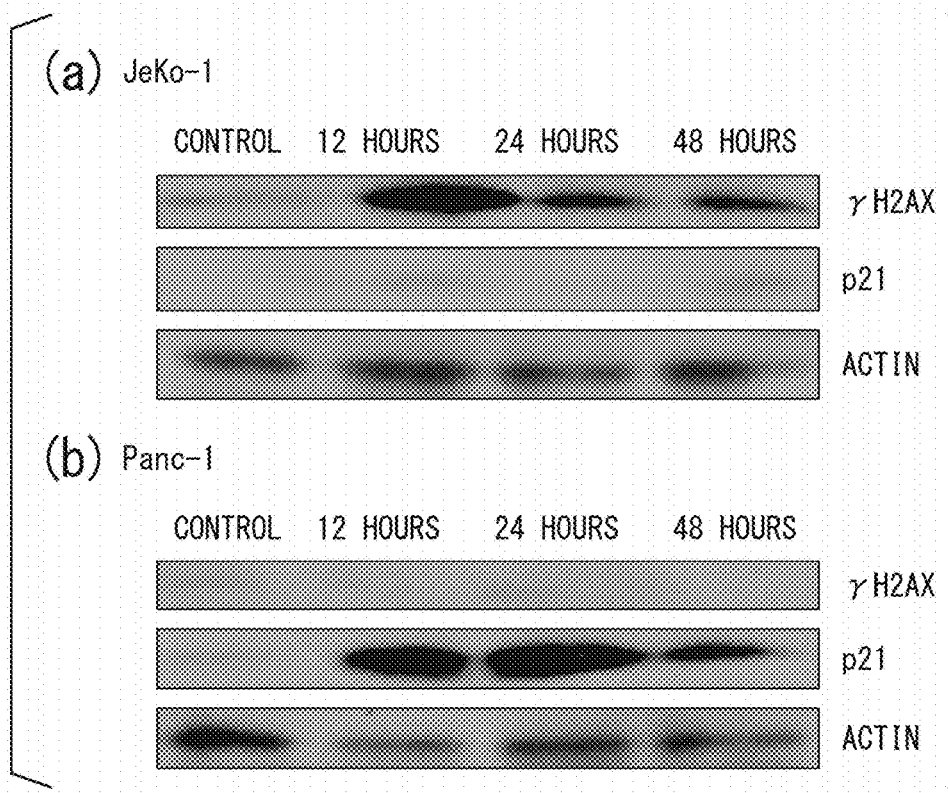
FIGS. 7(a) and 7(b) are photographs showing results of Western blotting in Experimental Example 7.

FIGS. 7(a) and 7(b) are photographs showing results of Western blotting. FIG. 7(a) shows results of JeKo-1 cells, and FIG. 7(h) shows results of Panc-1 cells. In FIGS. 7(a) and 7(b), "γH2AX" represents a result of detecting the presence of phosphorylated H2AX, and "p21" represents a result of detecting the presence of p21 protein.

As a result, in the JeKo-1 cells, phosphorylation of H2AX was detected 12 hours after 3EZ,20Ac-ingenol treatment, and it was confirmed that a DNA damage response was induced. On the other hand, in the Panc-1 cells, phosphorylation of H2AX was not detected. However, in the Panc-1 cells, induction of a high expression level of p21 protein was observed, this protein being known to select which one of cell proliferation inhibition or apoptosis will proceed after DNA damage response.

As will be described later, it became clear that JeKo-1 cells and Panc-1 cells are cells having a large abundance of cyclin D1 protein. For this reason, it could be confirmed that administration of 3EZ,20Ac-ingenol, which does not cause DNA cleavage, causes an increase in phosphorylation of H2AX in JeKo-1 cells, and causes an increase in expression of p21 protein in Panc-1 cells 12 hours after 3EZ,20Ac-ingenol treatment. Furthermore, as described above, activation of caspase 3 was recognized 12 hours after 3EZ,20Ac-ingenol treatment. That is, it could be confirmed that the activation of the caspase 3 occurred at the same time as the expression of the p21 protein. Thereafter, a rapid decrease in p21 protein was recognized 48 hours after 3EZ,20Ac-ingenol treatment.

Based on these results, it became clear that, when Panc-1 cells, which are cells derived from pancreatic cancer and which are resistant to an anticancer agent, are treated with 3EZ,20Ac-ingenol, this activates caspase 3 by p21 protein expression. In addition, it was thought that the activated caspase 3 decomposed the p21 protein and acted to direct inducing of apoptosis. This is a mechanism in which administration of 3EZ,20Ac-ingenol that does not cause DNA cleavage induces DNA damage response, inhibits cell proliferation, and induces apoptosis.

In addition, in normal cells, since an excess amount of cyclin D1 is not present, administration of 3EZ,20Ac-ingenol does not inhibit proliferation or induce apoptosis.

Experimental Example 8

(Examination of Expression of ATR and p53 Proteins by 3EZ,20Ac-Ingenol Treatment)

3EZ,20Ac-ingenol is a compound that does not generate a damage monitoring mechanism due to DNA cleavage damage in classifications of the related art. However, based on the above-described results of the experimental examples, it became clear that apoptosis was induced by 3EZ,20Ac-ingenol treatment of BALL-1, JeKo-1 and Panc-1 cells. Accordingly, expression of proteins regarding signal transmission induced by DNA damage response was examined by Western blotting.

Specifically, JeKo-1 cells were cultured for 0 (control), 12, 24, and 48 hours in the presence of 0.5 μM of 3EZ,20Ac-ingenol. In addition, Panc-1 cells were cultured for 0 (control), 12, 24, and 48 hours in the presence of 3 μM of 3EZ,20Ac-ingenol.

Subsequently, ATR protein, p53 protein, and phosphorylated p53 (hereinafter also referred to as "p-p53") protein in the respective cells were respectively detected using an anti-ATR antibody (Cell Signaling Technology), an anti-p53 antibody (Santa Cruz), and an anti-p-p53 antibody (Cell Signaling Technology). Furthermore, as a loading control, actin protein was detected using an anti-actin antibody (Sigma).

Figure 8:
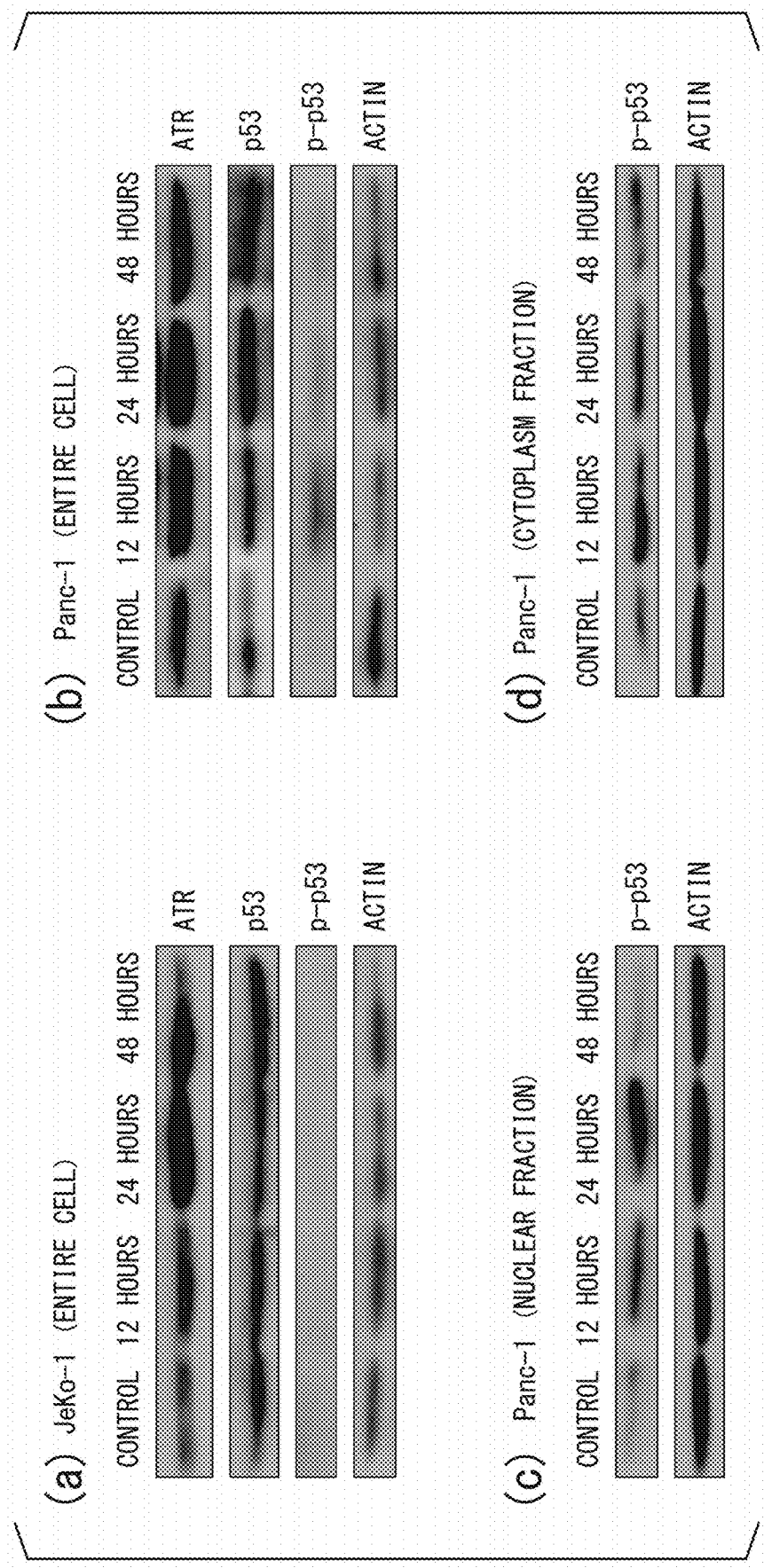
FIGS. 8(a) to 8(d) are photographs showing results of Western blotting in Experimental Example 8.

FIGS. 8(a) to 8(d) are photographs showing results of Western blotting. FIG. 8(a) shows results of JeKo-1 cells (entire cells), FIG. 8(b) shows results of Panc-1 cells (entire cells), and FIG. 8(c) shows results of Panc-1 cells (a nuclear fraction), and FIG. 8(d) shows results of Panc-1 cells (a cytoplasm fraction).

As a result, in both JeKo-1 cells and Panc-1 cells, an increase in expression level of ATR protein was recognized 12 hours after 3EZ,20Ac-ingenol treatment, a further increase therein was recognized 24 hours after the treatment, and a decrease was recognized 48 hours after the treatment.

In both JeKo-1 cells and Panc-1 cells, an increase in expression level of p53 protein was recognized 12 hours after 3EZ,20Ac-ingenol treatment, and an increase in expression level was recognized until 48 hours after the treatment.

In addition, in the JeKo-1 cells, phosphorylation of p53 was not confirmed, but in the Panc-1 cells, phosphorylation of p53 was observed 12 hours after 3EZ,20Ac-ingenol treatment. Furthermore, based on the results of FIGS. 8(c) and 8(d), it became clear that the amount of phosphorylated p53 protein increased in both the nuclear fraction and the cytoplasm fraction of the Panc-1 cells.

Based on the above results, it became clear that, in the JeKo-1 cells and the Panc-1 cells, 3EZ,20Ac-ingenol treatment enhanced DNA damage response, induced expression of ATR protein, and increased a concentration of p53 protein in the cells. Furthermore, it is thought that, in the Panc-1 cells, phosphorylation of p53 occurred, and a strong level of induction of apoptosis occurred.

Accordingly, it became clear that, when Panc-1 cells, which are cells derived from pancreatic cancer and which are resistant to an anticancer agent, are treated with 3EZ, 20Ac-ingenol, not only the above-described apoptosis induction occurs due to caspase 3 activation by the expression of p21 protein, but also apoptosis induction occurs due to p53 activation by ATR protein.

Experimental Example 9

(Examination of siRNA against ATR)

The effects of 3EZ,20Ac-ingenol treatment on expression of ATR were examined. First, BALL-1 cells were cultured in the presence of 3EZ,20Ac-ingenol at a final concentration of 0.5 μM for 12, 24, and 48 hours, and an expression level of ATR protein was analyzed by Western blotting using an anti-ATR antibody (Santa Cruz). Cells cultured in the absence of 3EZ,20Ac-ingenol were used as controls.

Figure 9:
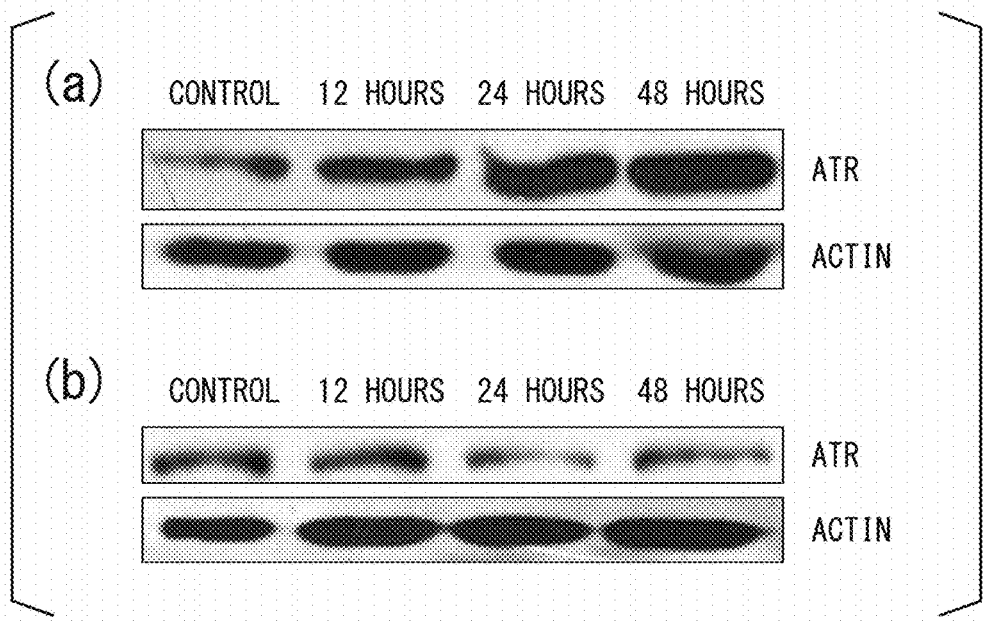
FIGS. 9(a) and 9(b) are photographs showing results of Western blotting in Experimental Example 9.

FIG. 9(a) shows photographs of results of Western blotting. Actin protein was detected as a loading control. As a result, it became clear that the expression of ATR increased from 12 hours after the start of 3EZ,20Ac-ingenol treatment of the BALL-1 cells, and continued until 48 hours after the start of the treatment.

Subsequently, siRNA against ATR ("ON-TARGET Plus Human ATR (545) siRNA-SMARTpool," GE Dharmacon) was introduced into BALL-1 cells at a final concentration of 50 nM and incubated for 48 hours. Subsequently, a cell medium was replaced with a new medium containing 3EZ, 20Ac-ingenol at a final concentration of 0.5 μM and culturing was performed for 12, 24, and 48 hours, and an expression level of ATR protein was analyzed by Western blotting using an anti-ATR antibody (Santa Cruz).

Cells into which control siRNA ("ON-TARGET Plus Nontargeting pool," GE Dharmacon) was introduced and which were then cultured in the absence of 3EZ,20Ac-ingenol were used as controls.

FIG. 9(b) shows photographs of results of Western blotting in the presence of siRNA. Actin protein was detected as a loading control. As a result, it was confirmed that, in the BALL-1 cells into which siRNA against ATR was introduced, an increase in ATR expression was not recognized even when the cells were treated with 3EZ,20Ac-ingenol.

Experimental Example 10

(Examination of Effect of ATR on Cell Proliferation Inhibition by 3EZ,20Ac-Ingenol Treatment)

An effect of ATR activity on cell proliferation inhibition was examined. In the same manner as in Experimental Example 9, siRNA against ATR was introduced into BALL-1 cells, and the cells were incubated for 48 hours. Subsequently, a cell medium was replaced with a medium containing 3EZ,20Ac-ingenol at a final concentration of 0.5 μM, and culturing was performed for 48 hours.

For comparison, BALL-1 cells cultured for 48 hours in a medium containing 3EZ,20Ac-ingenol at a final concentration of 0.5 μM without introduction of siRNA were used. In addition, as controls, cells into which control siRNA ("ON-TARGET Plus Nontargeting pool," GE Dharmacon) was introduced and which were then cultured in the absence of 3EZ,20Ac-ingenol were used.

Figure 10:
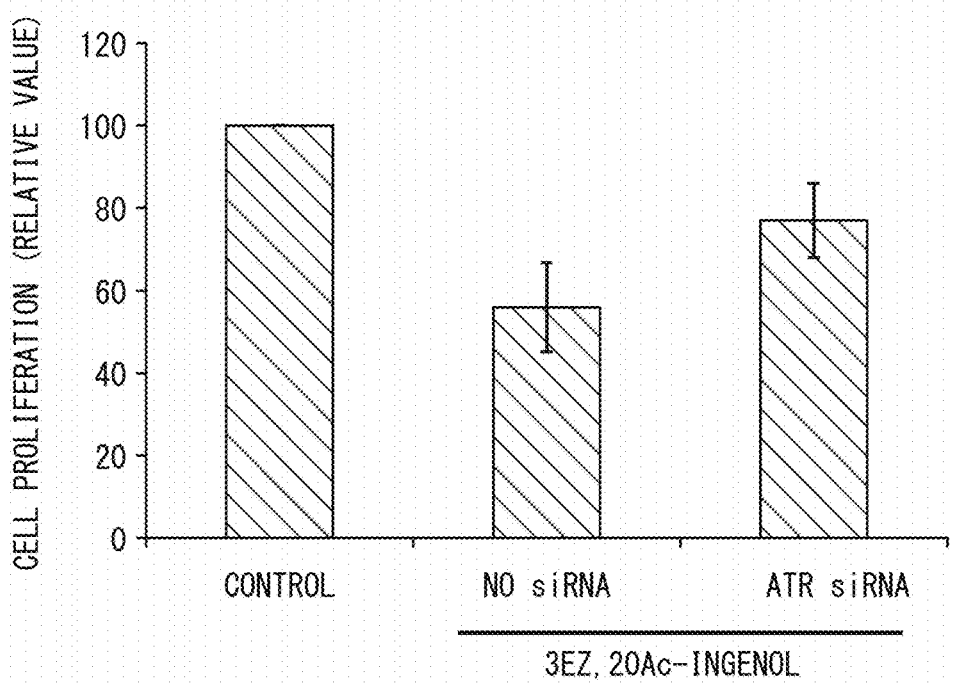
FIG. 10 is a graph showing results of MTT assay in Experimental Example 10.

FIG. 10 is a graph showing results of measuring cell proliferation by MTT assay. As a result, it became clear that cell proliferation inhibition was reduced by about 20% by knockdown of ATR.

Based on these results, it became clear that cell proliferation inhibition by 3EZ,20Ac-ingenol is ATR-dependent.

Experimental Example 11

(Examination of Effect of 3EZ,20Ac-Ingenol Treatment on Phosphorylation of Akt Protein)

The effect of 3EZ,20Ac-ingenol treatment on a PI3K/Akt signaling pathway was examined. Specifically, BALL-1 cells, TKG0210 cells, and TKG0377 cells were cultured for 48 hours in the presence of 3EZ,20Ac-ingenol at a final concentration of 0.5 μM, and by Western blotting using an anti-p-Akt (Ser$^{473}$) antibody (Cell Signaling Technology), phosphorylation of the 473th serine residue of an Akt protein in respective fractions of the entire cell, a nucleus, and a cytoplasm was analyzed. In addition, cells cultured in the absence of 3EZ,20Ac-ingenol were used as controls.

Figure 11:
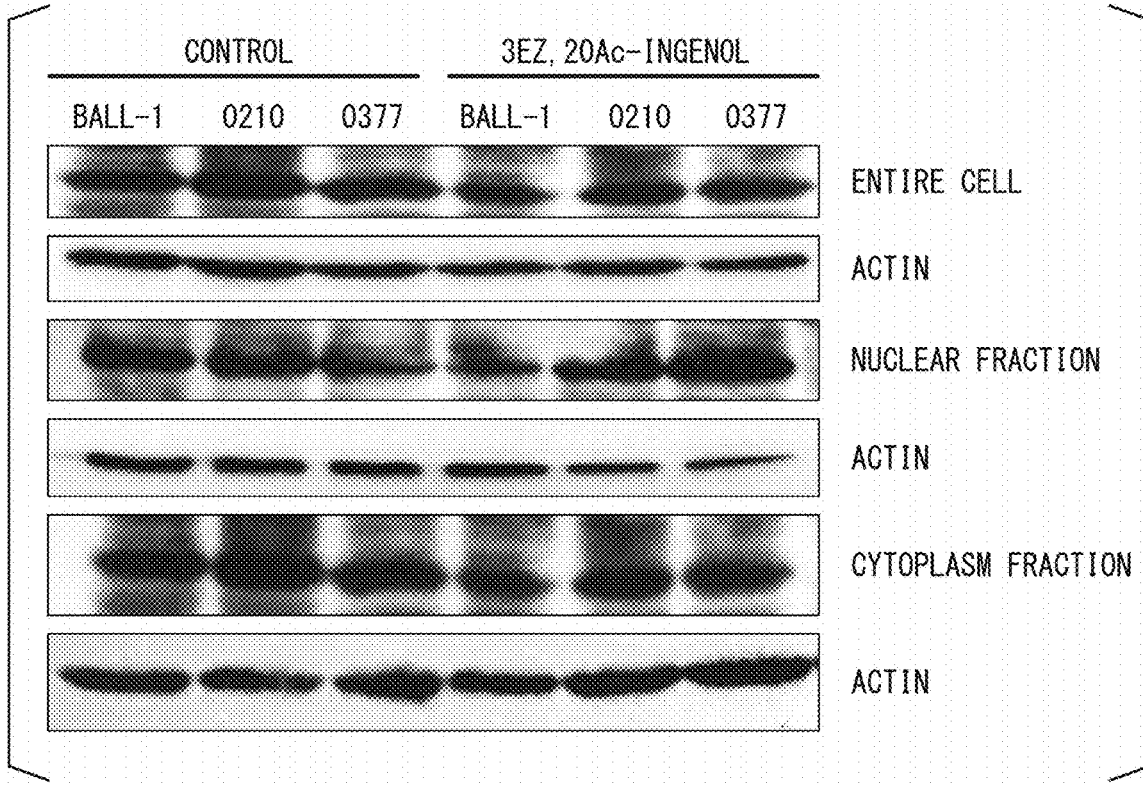
FIG. 11 shows photographs of results of Western blotting in Experimental Example 11.

FIG. 11 shows photographs of results of Western blotting. Actin protein was detected as a loading control. As a result, in the entire cell debris of the BALL-1 cells (a lane 4) and the entire cell debris of the TKG0210 cells (a lane 5), a decrease in abundance of phosphorylated Akt (Ser$^{473}$) (hereinafter also referred to as "p-Akt") was recognized.

In addition, the decrease in abundance of p-Akt in the entire cell debris of the BALL-1 cells was small, but it became clear that an abundance of p-Akt in the nuclear fraction of the BALL-1 cells was significantly decreased (a lane 4). In contrast, an abundance of p-Akt in the nuclear fraction of the TKG0210 cells remained almost unchanged even after 3EZ,20Ac-ingenol treatment was performed. Furthermore, it became clear that an abundance of p-Akt in the nuclear fraction of the TKG0377 cells was increased by 3EZ,20Ac-ingenol treatment.

In addition, an abundance of p-Akt in the cytoplasm fraction of the TKG0210 cells and the TKG0377 cells remained almost unchanged even after 3EZ,20Ac-ingenol treatment was performed. In contrast, an abundance of p-Akt in the cytoplasm fraction of the BALL-1 cells was slightly reduced by 3EZ,20Ac-ingenol treatment.

Experimental Example 12

(Examination of Effect of 3EZ,20Ac-Ingenol Treatment of BALL-1 Cells on PTEN, p-PTEN, and p-Akt)

The effect of 3EZ,20Ac-ingenol treatment on PTEN, p-PTEN, and p-Akt of BALL-1 cells was examined. First, BALL-1 cells were cultured for 3, 6, 12, 24, and 48 hours in the presence of 3EZ,20Ac-ingenol at a final concentration of 0.5 μM, and by Western blotting using an anti-PTEN antibody (Santa Cruz), an anti-p-PTEN (Ser$^{380}$/Thr$^{382/383}$) antibody (Santa Cruz), and an anti-p-Akt (Ser$^{473}$) antibody (Cell Signaling Technology), abundances of PTEN, p-PTEN, and p-Akt in the entire cell fraction were analyzed. In addition, cells cultured in the absence of 3EZ,20Ac-ingenol were used as controls.

Figure 12:
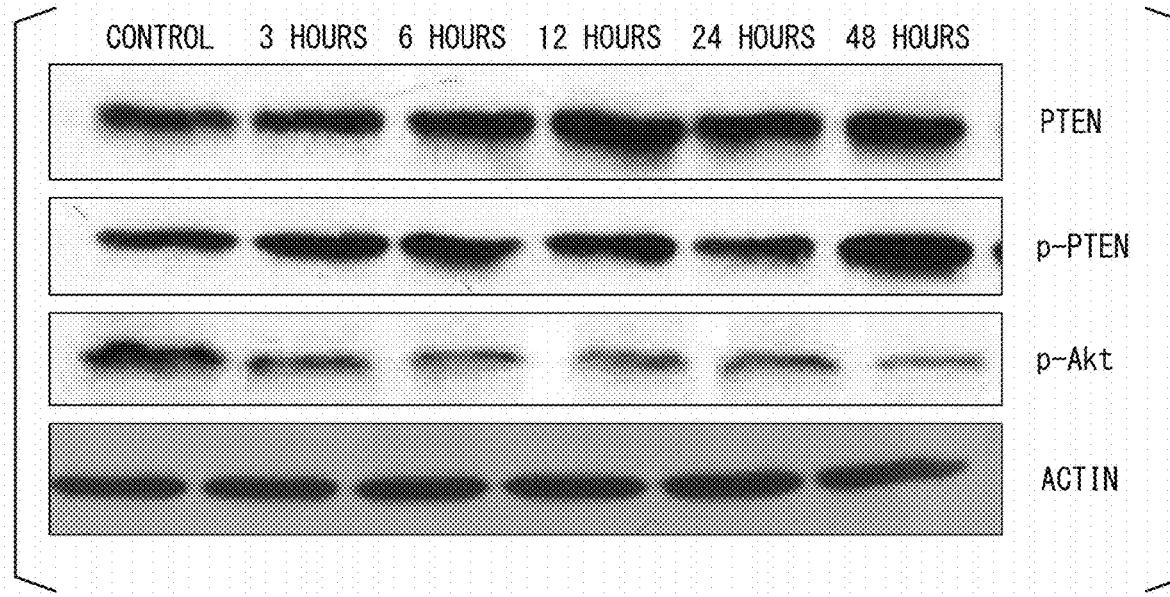
FIG. 12 shows photographs of results of Western blotting in Experimental Example 12.

FIG. 12 shows photographs of results of Western blotting. Actin protein was detected as a loading control. As a result, an increase in abundance of PTEN due to 3EZ,20Ac-ingenol treatment was observed. In addition, an abundance of p-PTEN increased in accordance with an increase in abundance of PTEN. As a result, down-regulation of p-Akt abundance was observed.

Experimental Example 13

(Examination of Effect of 3EZ,20Ac-Ingenol Treatment of JeKo-1 Cells and Panc-1 Cells on PTEN)

The effect of 3EZ,20Ac-ingenol treatment on expression of PTEN in JeKo-1 cells and Panc-1 cells was examined.

Specifically, first, JeKo-1 cells were cultured for 0 (control), 12, 24, and 48 hours in the presence of 0.5 μM of 3EZ,20Ac-ingenol. In addition, Panc-1 cells were cultured for 0 (control), 12, 24, and 48 hours in the presence of 3 μM of 3EZ,20Ac-ingenol.

Subsequently, abundances of PTEN protein in entire cell fractions, nuclear fractions, and cytoplasm fractions of the respective cells were analyzed by Western blotting using an anti-PTEN antibody (Santa Cruz). Furthermore, as a loading control, actin protein was detected using an anti-actin antibody (Sigma).

Figure 13:
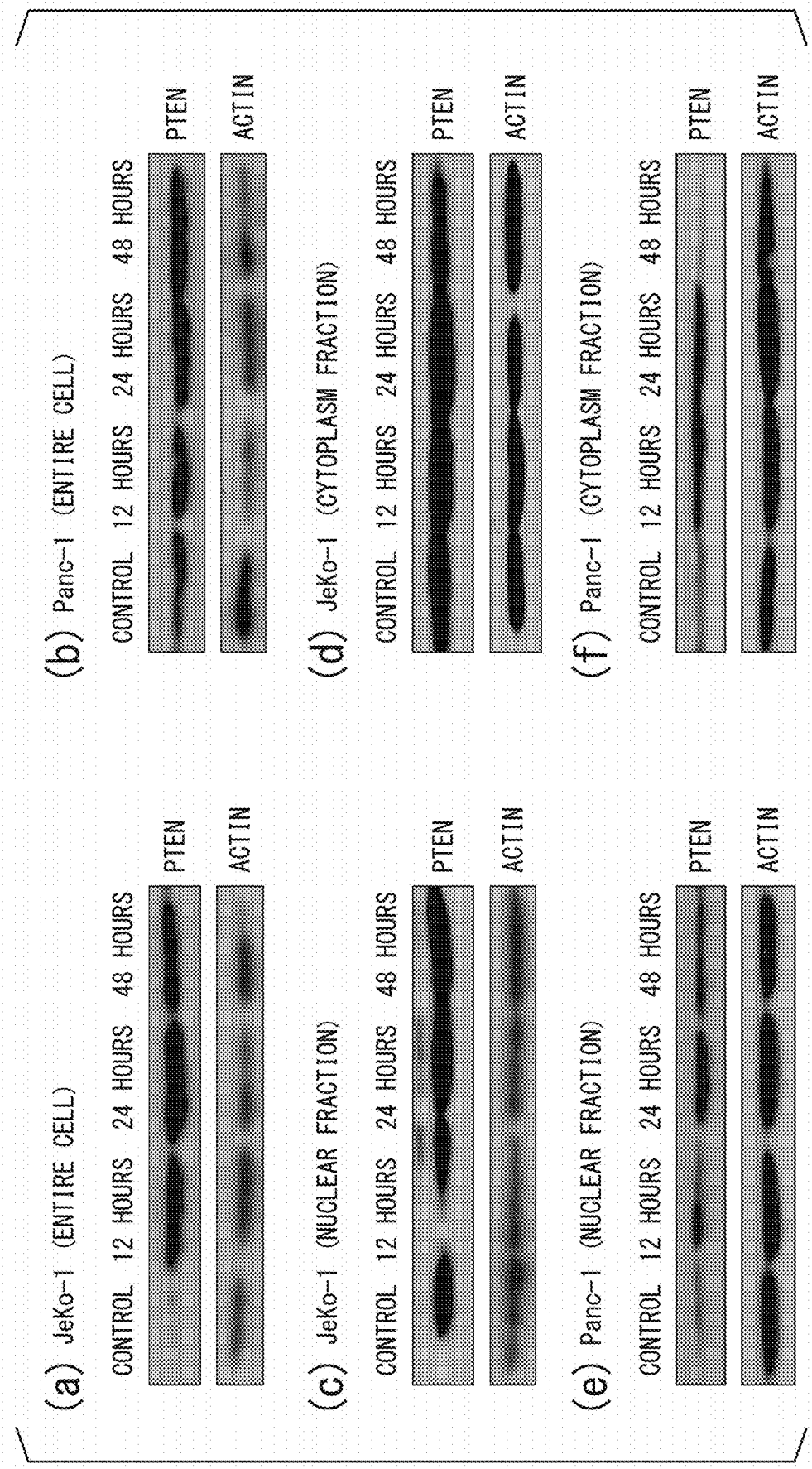
FIGS. 13(a) to 13(f) are photographs showing results of Western blotting in Experimental Example 13.

FIGS. 13(a) to 13(f) are photographs showing results of Western blotting. FIG. 13(a) shows results of JeKo-1 cells (the entire cell), FIG. 13(b) shows results of Panc-1 cells (the entire cell), FIG. 13(c) shows results of JeKo-1 cells (a nuclear fraction), FIG. 13(d) shows results of JeKo-1 cells (a cytoplasm fraction), FIG. 13(e) shows results of Panc-1 cells (a nuclear fraction), and FIG. 13(f) shows results of Panc-1 cells (a cytoplasm fraction).

As a result, in both JeKo-1 cells and Panc-1 cells, an abundance of PTEN protein increased in the entire cell fractions 12 hours after 3EZ,20Ac-ingenol treatment, and a high expression level was observed until 48 hours after the treatment. In both JeKo-1 cells and Panc-1 cells, an increase in abundance of PTEN protein in the nuclear fraction was observed 12 hours to 24 hours after 3EZ,20Ac-ingenol treatment. In addition, in both JeKo-1 cells and Panc-1 cells, an increase in abundance of PTEN protein in the cytoplasm fraction was observed 12 hours to 24 hours after 3EZ,20Ac-ingenol treatment, but a decrease in abundance of PTEN protein was observed 48 hours after the treatment.

It is known that cytoplasmic PTEN inhibits p-Akt and induces apoptosis, and PTEN in the nucleus inhibits phosphorylation of ERK and cyclin D1 and acts to inhibit cell proliferation. Based on the above results, it became clear that an increase in abundance of PTEN protein due to 3EZ,20Ac-ingenol treatment acts on both induction of apoptosis and inhibition of cell proliferation.

Experimental Example 14

(Examination of Effect of 3EZ,20Ac-Ingenol Treatment of BALL-1 Cells on p-Akt)

BALL-1 cells, TKG0210 cells, and TKG0377 cells were cultured for 24 and 48 hours in the presence of 3EZ,20Ac-ingenol at a final concentration of 0.5 μM, and abundances of p-Akt in the nuclear fraction and the cytoplasm fraction were analyzed by Western blotting. In addition, respective cells cultured in the absence of 3FZ,20Ac-ingenol were used as controls.

Figure 14:
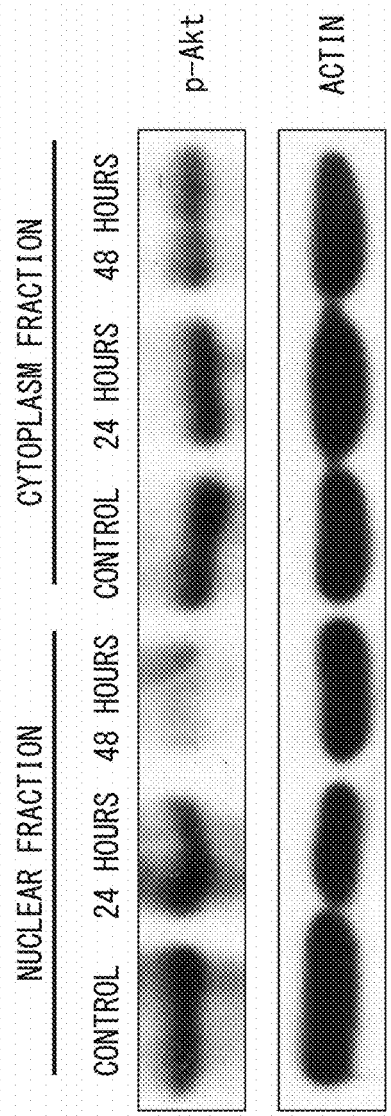
FIGS. 14(a) and 14(b) are photographs showing results of Western blotting in Experimental Example 14.
Figure 14:
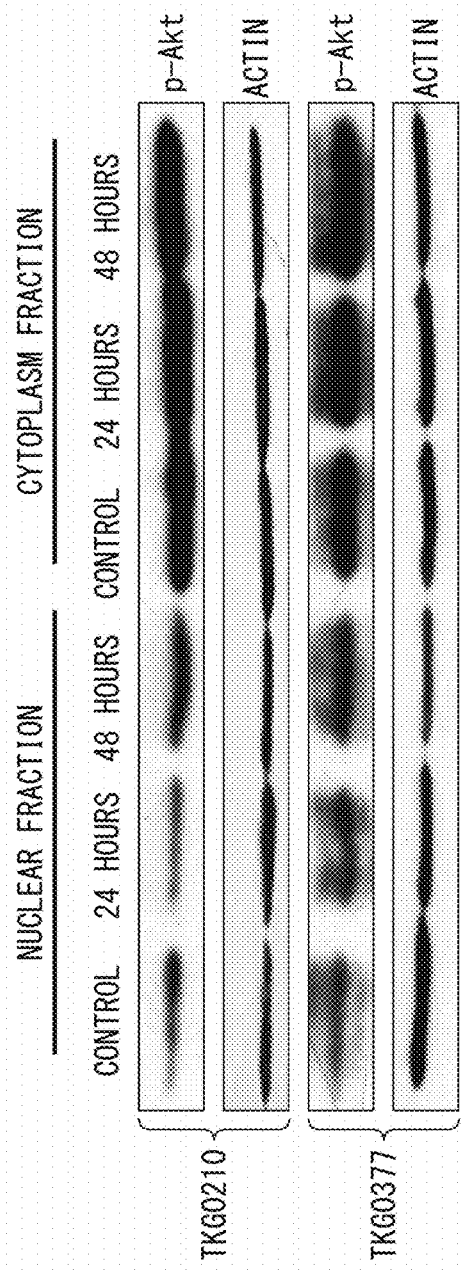

FIG. 14(a) shows photographs of results of Western blotting on BALL-1 cells. Actin protein was detected as a loading control. As a result, in the BALL-1 cells, a slight decrease in abundance of p-Akt was observed in the cytoplasm fraction 48 hours after 3EZ,20Ac-ingenol treatment. In addition, a moderate decrease in abundance of p-Akt was observed in the nuclear fraction 24 hours after 3EZ,20Ac-ingenol treatment, and a further decrease in abundance of p-Akt in the nuclear fraction was observed 48 hours after 3EZ,20Ac-ingenol treatment.

Meanwhile, FIG. 14(b) shows photographs of results of Western blotting on TKG0210 cells and TKG0377 cells. Actin protein was detected as a loading control. As a result, unlike the results of the BALL-1 cells, no decrease in abundance of p-Akt was observed in the cytoplasm fraction and nuclear fraction of the TKG0210 cells and TKG0377 cells.

Experimental Example 15

(Examination of Effect of 3EZ,20Ac-Ingenol Treatment of JeKo-1 Cells and Panc-1 Cells on p-Akt)

The effect of 3EZ,20Ac-ingenol treatment on p-Akt in JeKo-1 cells and Panc-1 cells was examined.

Specifically, first, JeKo-1 cells were cultured for 0 (control), 12, 24, and 48 hours in the presence of 0.5 μM of 3EZ,20Ac-ingenol. In addition, Panc-1 cells were cultured for 0 (control), 12, 24, and 48 hours in the presence of 3 μM of 3EZ,20Ac-ingenol.

Subsequently, by Western blotting using an anti-Akt antibody (Cell Signaling Technology) and an anti-p-Akt (Ser$^{473}$) antibody (Cell Signaling Technology), abundances of total amounts of Akt protein and p-Akt in the entire cell fractions, nuclear fractions, and cytoplasm fractions of the respective cells were analyzed. Furthermore, as a loading control, actin protein was detected using an anti-actin antibody (Sigma).

Figure 15:
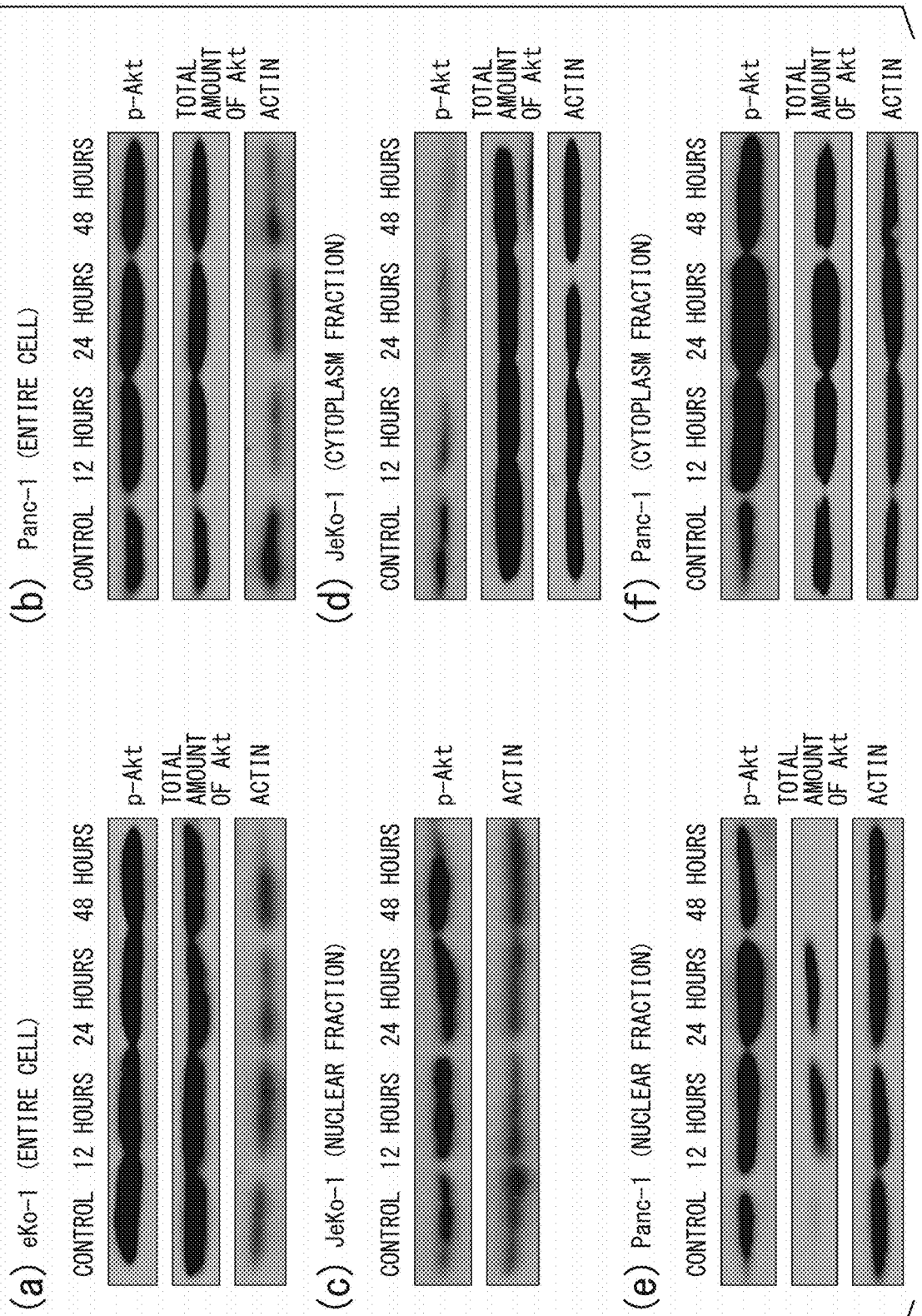
FIGS. 15(a) to 15(f) are photographs showing results of Western blotting in Experimental Example 15.

FIGS. 15(a) to 15(f) are photographs showing results of Western blotting. FIG. 15(a) shows results of JeKo-1 cells (the entire cell), FIG. 15(b) shows results of Panc-1 cells (the entire cell), FIG. 15(c) shows results of JeKo-1 cells (a nuclear fraction), FIG. 15(d) shows results of JeKo-1 cells (a cytoplasm fraction), FIG. 15(e) shows results of Panc-1 cells (a nuclear fraction), and FIG. 15(f) shows results of Panc-1 cells (a cytoplasm fraction).

As a result, a slight decrease in abundance of p-Akt was observed in the entire cell fraction of the JeKo-1 cells by 3EZ,20Ac-ingenol treatment, and almost no change was observed in an abundance of a total amount of Akt. In addition, in the entire cell fraction of the Panc-1 cells, a temporary increase in abundances of both p-Akt and total amount of Akt was recognized 12 hours and 24 hours after 3EZ,20Ac-ingenol treatment, but a decrease was observed again 48 hours after the treatment. Furthermore, in the nuclear fraction of the JeKo-1 cells, no change in an abundance of p-Akt was recognized even after 3EZ,20Ac-ingenol treatment was performed. On the other hand, in the cytoplasm fraction of the JeKo-1 cells, a decrease in abundance of p-Akt was clearly recognized 12 to 48 hours after 3EZ,20Ac-ingenol treatment. Furthermore, in both the nuclear fraction and the cytoplasm fraction of the Panc-1 cells, an increase in abundance of both p-Akt and total amount of Akt was recognized 12 to 24 hours after 3EZ,20Ac-ingenol treatment, but a decrease was observed 48 hours after the treatment.

Experimental Example 16

(Examination of Effect of 3EZ,20Ac-Ingenol Treatment of on PTEN and p-Akt)

The effect of 3EZ,20Ac-ingenol treatment on PTEN and p-Akt was examined using siRNA against PTEN. First, BALL-1 cells were cultured for 12, 24, and 48 hours in the presence of 3EZ,20Ac-ingenol at a final concentration of 0.5 μM, and an abundance of p-Akt was analyzed by Western blotting in the same manner as in Experimental Example 11. Cells cultured in the absence of 3EZ,20Ac-ingenol were used as controls.

Figure 16:
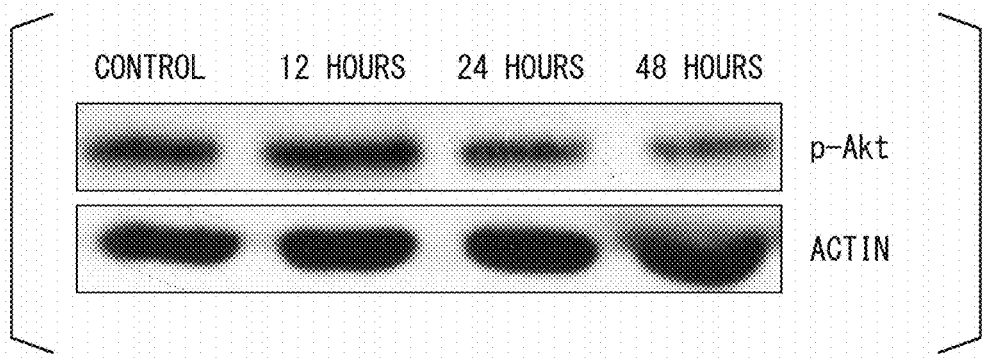
FIG. 16 shows photographs of results of Western blotting in Experimental Example 16.

FIG. 16 shows photographs of results of Western blotting. Actin protein was detected as a loading control. As a result, it became clear that an abundance of p-Akt in the BALL-1 cells decreased 24 hours after the start of 3EZ,20Ac-ingenol treatment of the BALL-1 cells.

Subsequently, siRNA against PTEN ("ON-TARGET Plus Human PTEN (5728) siRNA-SMARTpool," GE Dharmacon) was introduced into BALL-1 cells at a final concentration of 50 nM and incubated for 48 hours. Subsequently, a cell medium was replaced with a new medium and cultured for 12, 24, and 48 hours in the presence or absence of 3EZ,20Ac-ingenol at a final concentration of 0.5 µM, and by Western blotting using an anti-PTEN antibody (Santa Cruz) and an anti-p-Akt (Ser$^{473}$) antibody (Cell Signaling Technology), abundances of PTEN protein and p-Akt were analyzed.

In addition, cells into which control siRNA ("ON-TARGET Plus Nontargeting pool," GE Dharmacon) was introduced and which were then cultured in the absence of 3EZ,20Ac-ingenol were used as controls.

Figure 17:
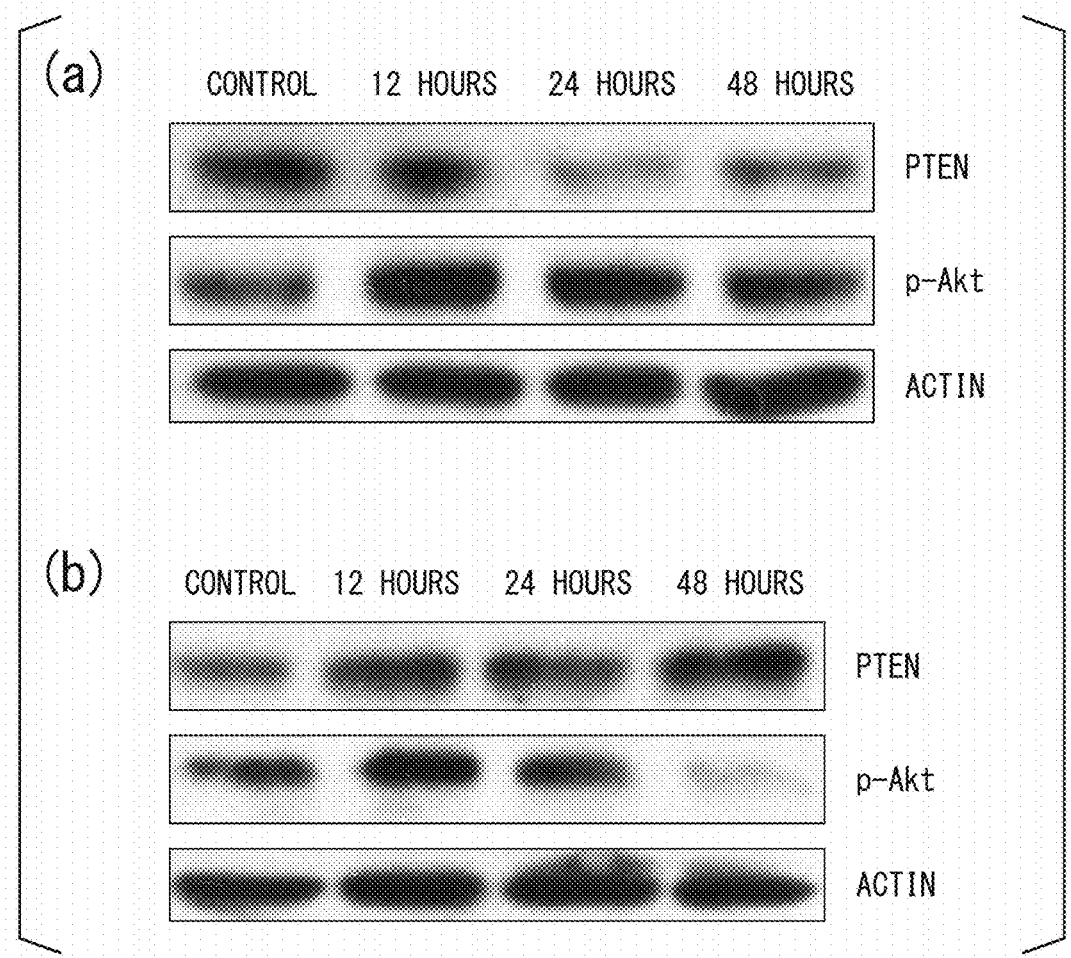
FIGS. 17(a) and 17(b) are photographs showing results of Western blotting in Experimental Example 16.

FIGS. 17(a) and 17(b) are photographs showing results of Western blotting. FIG. 17(a) shows results of introducing siRNA against PTEN into cells, and then culturing the cells in the absence of 3EZ,20Ac-ingenol. In addition, FIG. 17(b) shows results of introducing siRNA against PTEN into cells, and then culturing the cells in the presence of 3EZ,20Ac-ingenol.

Actin protein was detected as a loading control. As a result, as shown in FIG. 17(a), in the cells in which siRNA against PTEN was introduced into BALL-1 cells, and these cells were then cultured in the absence of 3EZ,20Ac-ingenol, a decrease in expression level of PTEN was observed 12 hours after culturing. This result indicates that the introduction of siRNA effectively inhibited the expression of PTEN.

In addition, as shown in FIG. 17(a), an abundance of p-Akt significantly increased in the BALL-1 cells in which the expression of PTEN was inhibited by the introduction of siRNA. This result indicates that PTEN dephosphorylates p-Akt in the BALL-1 cells.

On the other hand, as shown in FIG. 17(b), in the cells in which siRNA against PTEN was introduced into BALL-1 cells, and these cells were then cultured in the presence of 3EZ,20Ac-ingenol at a final concentration of 0.5 µM, an increase in expression level of PTEN was observed 12 hours after culturing, and an expression level of PTEN further increased 24 hours and 48 hours after culturing.

In addition, as shown in FIG. 17(b), in the BALL-1 cells in which the expression of PTEN was inhibited by introduction of siRNA and on which 3EZ,20Ac-ingenol treatment was performed, an increase in abundance of p-Akt was observed after 12 hours. However, a decrease in abundance of p-Akt was observed after 24 hours and 48 hours.

Based on the above results, it became clear that 3EZ, 20Ac-ingenol down-regulates an abundance of p-Akt by up-regulating PTEN.

Experimental Example 17

(Examination of Expression of Cyclin D1 in BALL-1 Cells, TKG0210 Cells and TKG0377 Cells)

Expression of cyclin D1 in BALL-1 cells, TKG0210 cells and TKG0377 cells was examined. Specifically, abundances of cyclin D1 in the entire cell fractions of the respective cells were analyzed by Western blotting using an anti-cyclin-D1 antibody (Santa Cruz).

Figure 18:
FIG. 18 shows photographs of results of Western blotting in Experimental Example 17.

FIG. 18 shows photographs of results of Western blotting. Actin protein was detected as a loading control. As a result, it became clear that BALL-1 cells overexpress cyclin D1.

On the other hand, expression of cyclin D1 was not recognized in the TKG0210 cells and the TKG0377 cells.

Experimental Example 18

(Examination of Expression of Cyclin D1 in JeKo-1 Cells and Panc-1 Cells)

Expression of cyclin D1 in JeKo-1 cells and Panc-1 cells was examined. Specifically, abundances of cyclin D1 in the entire cell fractions of the respective cells were analyzed by Western blotting using an anti-cyclin-D1 antibody (Santa Cruz).

Figure 19:
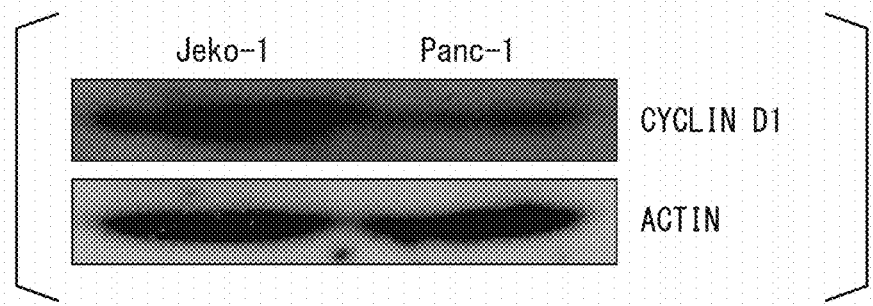
FIG. 19 shows photographs of results of Western blotting in Experimental Example 18.

FIG. 19 shows photographs of results of Western blotting. Actin protein was detected as a loading control. As a result, it became clear that cyclin D1 was excessively overexpressed in the JeKo-1 cells, and cyclin D1 was also overexpressed in the Panc-1 cells.

Experimental Example 19

(Examination of Effect of 3EZ,20Ac-Ingenol Treatment on Expression of Cyclin D1 in BALL-1 Cells)

The effect of 3EZ,20Ac-ingenol treatment on expression of cyclin D1 in BALL-1 cells was examined.

Specifically, BALL-1 cells were cultured for 12, 24, and 48 hours in the presence of 3EZ,20Ac-ingenol at a final concentration of 0.5 µM, and abundances of cyclin D1 in the nuclear fraction and the cytoplasm fraction were analyzed by Western blotting. In addition, cells cultured in the absence of 3EZ,20Ac-ingenol were used as controls.

Figure 20:
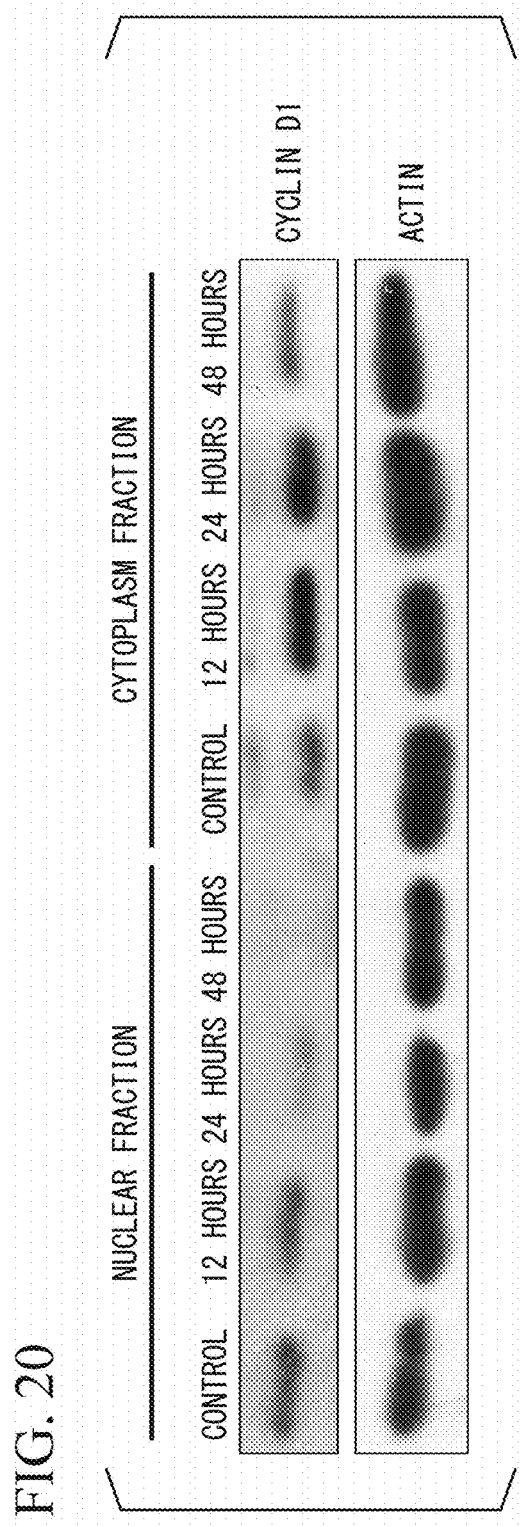
FIG. 20 shows photographs of results of Western blotting in Experimental Example 19.

FIG. 20 shows photographs of results of Western blotting. Actin protein was detected as a loading control. As a result, it became clear that a large amount of cyclin D1 was present in the nuclear fraction of the control BALL-1 cells. In addition, a decrease in abundance of cyclin D1 was observed in the nuclear fraction 24 hours after 3EZ,20Ac-ingenol treatment.

On the other hand, it became clear that only a small amount of cyclin D1 was present in the cytoplasm fraction of the control BALL-1 cells. Furthermore, it became clear that an abundance of cyclin D1 in the cytoplasm fraction increased 12 hours and 24 hours after 3EZ,20Ac-ingenol treatment, and decreased again after 48 hours.

These results indicate that cyclin D1, which was present in the nucleus, transferred to the cytoplasm and decomposed in the cytoplasm due to treating the BALL-1 cells with 3EZ,20Ac-ingenol.

Experimental Example 20

(Examination of Effect of 3EZ,20Ac-Ingenol Treatment on Expression of Cyclin D1 in JeKo-1 Cells and Panc-1 Cells)

The effect of 3EZ,20Ac-ingenol treatment on expression of cyclin D1 in JeKo-1 cells and Panc-1 cells was examined.

Specifically, first, JeKo-1 cells were cultured for 0 (control), 12, 24, and 48 hours in the presence of 0.5 µM of 3EZ,20Ac-ingenol. In addition, Panc-1 cells were cultured for 0 (control), 12, 24, and 48 hours in the presence of 3 µM of 3EZ,20Ac-ingenol.

Subsequently, abundances of cyclin D1 in entire cell fractions, nuclear fractions, and cytoplasm fractions of the respective cells were analyzed by Western blotting.

Figure 21:
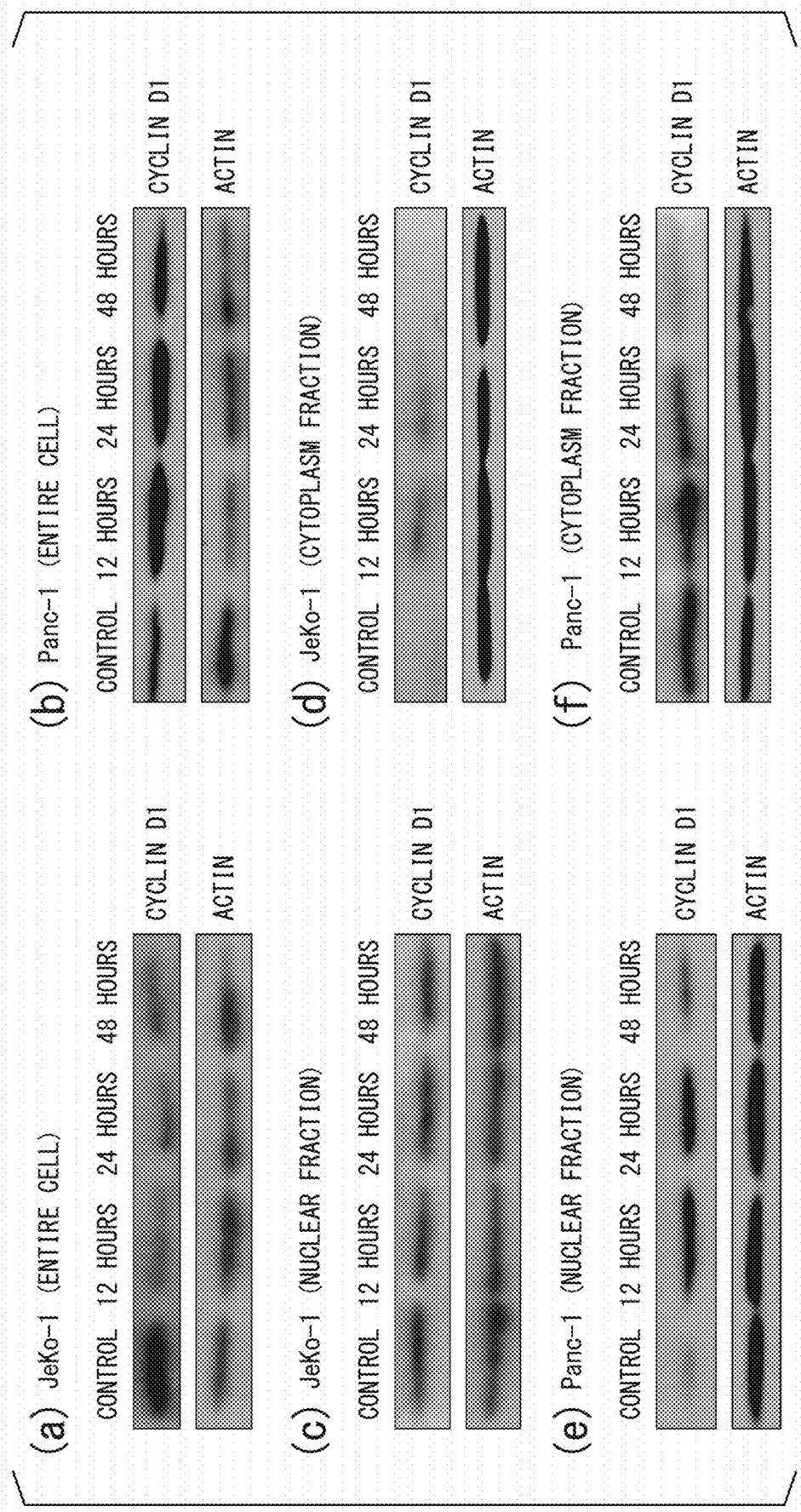
FIGS. 21(a) to 21(f) are photographs showing results of Western blotting in Experimental Example 20.

FIGS. 21(a) to 21(f) are photographs showing results of Western blotting. FIG. 21(a) shows results of JeKo-1 cells (the entire cell), FIG. 21(b) shows results of Panc-1 cells (the entire cell), FIG. 21(c) shows results of JeKo-1 cells (a nuclear fraction), FIG. 21(*d*) shows results of JeKo-1 cells (a cytoplasm fraction), FIG. 21(*e*) shows results of Panc-1 cells (a nuclear fraction), and FIG. 21(*f*) shows results of Panc-1 cells (a cytoplasm fraction).

As a result, in the entire cell fraction of the JeKo-1 cells, a decrease in expression level of cyclin D1 was observed 12 to 48 hours after 3EZ,20Ac-ingenol treatment. In addition, it became clear that, in the entire cell fraction of the Panc-1 cells, an expression level of cyclin D1 temporarily increased 12 to 24 hours after 3EZ,20Ac-ingenol treatment and then decreased thereafter.

In addition, in the nuclear fraction of the JeKo-1 cells, a slight decrease in expression level of cyclin D1 was observed 12 to 48 hours after 3EZ,20Ac-ingenol treatment. In addition, the presence of cyclin D1 was not detected in the cytoplasm fraction of the control JeKo-1 cells, but an increase in abundance of cyclin D1 was recognized 12 to 48 hours after 3EZ,20Ac-ingenol treatment, and a decrease was recognized thereafter.

In addition, in the nuclear fraction of the Panc-1 cells, it was observed that an expression level of cyclin D1 temporarily increased 12 hours after 3EZ,20Ac-ingenol treatment and decreased after 24 hours. Furthermore, in the cytoplasm fraction of the control Panc-1 cells, it became clear that although a large amount of cyclin D1 was detected, an abundance of cyclin D1 decreased 12 to 48 hours after 3EZ,20Ac-ingenol treatment.

It became clear that, in both JeKo-1 cells and Panc-1 cells, the 3EZ,20Ac-ingenol treatment eventually reduces an abundance of cyclin D1 or eliminates cyclin D1 in both the nuclear fraction and the cytoplasm fraction.

Based on the above results, it is thought that, GSK-3β was activated in accordance with a decrease in abundance of p-Akt, which leaded to phosphorylation of cyclin D1 in the nucleus, and as a result, the cyclin D1 transferred from the nucleus into the cytoplasm and decomposed due to proteasomes in the cytoplasm. Both cell lines derived from mantle cell lymphoma and pancreatic cancer are known to induce proliferation inhibition and cell death by knockdown of a cyclin D1 gene. Accordingly, also in the JeKo-1 cells and the Panc-1 cells, it is thought that a decrease in abundance of cyclin D1 affected proliferation inhibition and cell death.

Experimental Example 21

(Examination of Effect of 3EZ,20Ac-Ingenol Treatment on Activation of GSK-3β in JeKo-1 Cells and Panc-1 Cells)

As described above, it became clear that p-Akt is inhibited by 3EZ,20Ac-ingenol treatment of JeKo-1 cells and Panc-1 cells. Accordingly, activation of GSK-3β which is located downstream of p-Akt and upstream of a decomposition reaction of cyclin D1, and which transfers cyclin D1 from the nucleus into the cytoplasm was examined.

Specifically, first, JeKo-1 cells were cultured for 0 (control), 12, 24, and 48 hours in the presence of 0.5 µM of 3EZ,20Ac-ingenol. In addition, Panc-1 cells were cultured for 0 (control), 12, 24, and 48 hours in the presence of 3 µM of 3EZ,20Ac-ingenol.

Subsequently, abundances of GSK-3β and p-GSK-3β in the respective cells were analyzed by Western blotting using an anti-GSK-3β antibody (Cell Signaling Technology) and an anti-p-GSK-3β (Ser$^9$) antibody (Cell Signaling Technology). Furthermore, as a loading control, actin protein was detected using an anti-actin antibody (Sigma).

Figure 22:
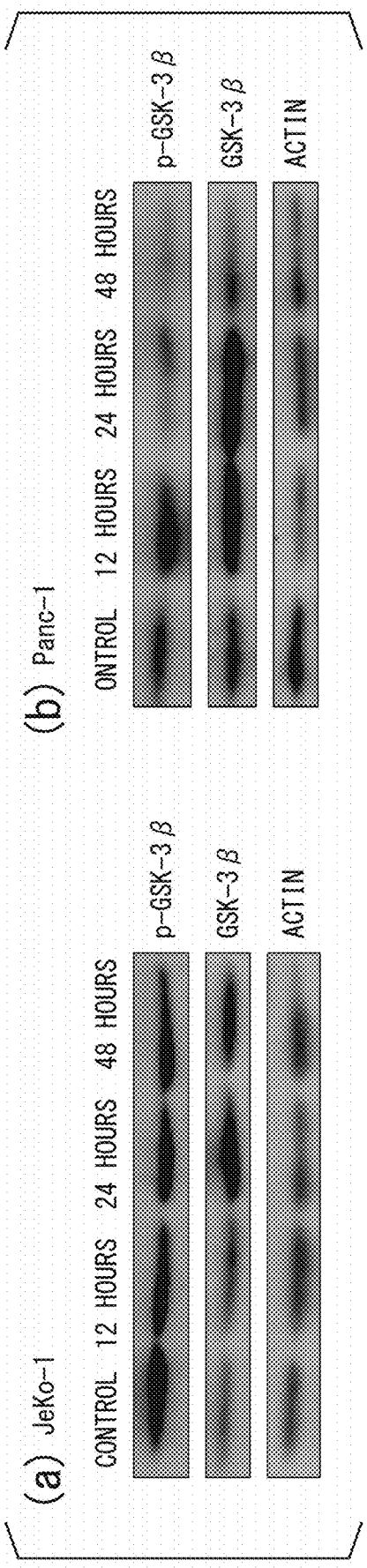
FIGS. 22(a) and 22(h) are photographs showing results of Western blotting in Experimental Example 21.

FIGS. 22(*a*) and 22(*b*) are photographs showing results of Western blotting. FIG. 22(*a*) shows results of JeKo-1 cells (the entire cell), and FIG. 22(*b*) shows results of Panc-1 cells (the entire cell).

As a result, in the JeKo-1 cells, an increase in GSK-3β was observed 24 hours after 3EZ,20Ac-ingenol treatment. In the Panc-1 cells, an increase in GSK-3β was observed 12 hours after 3EZ,20Ac-ingenol treatment. In addition, in both the JeKo-1 cells and the Panc-1 cells, a decrease in p-GSK-3β (an inactive type) was observed, and an increase in GSK-3β (an active type) was observed.

Based on the above results, it became clear that, by treating BALL-1 cells, JeKo-1 cells, and Panc-1 cells with 3EZ. 20Ac-ingenol, PTEN is activated, p-Akt is inhibited as a result, GSK-3β is activated as a result, cyclin D1 is phosphorylated as a result, the cyclin D1 is transferred from the nucleus into the cytoplasm, and thereby the cyclin D1 is decomposed.

In addition, in the Panc-1 cells, a temporary increase in abundance level of cyclin D1 was observed after 3EZ,20Ac-ingenol treatment. This indicates that, because cyclin D1 is present in the nucleus of the Panc-1 cells, a DNA replication factor remains undecomposed, and cyclin D1 is used for re-replication, thereby resulting in an enhanced DNA damage response. It is thought that an abundance level of cyclin D1 was observed to be temporarily increased because cyclin D1 is used during this re-replication in the inducing of a DNA damage response due to 3EZ,20Ac-ingenol treatment. Meanwhile, a decrease in abundance of p-GSK-3β and an increase in abundance of GSK-3β were consistently observed over time.

As shown above, 3EZ,20Ac-ingenol treatment induced a temporary increase in abundance of p-Akt. Increases in abundance of p-Akt and p-GSK-3β (an inactive type) were also observed in DNA damage due to administration of other compounds. In order to inhibit p-Akt, it is necessary to activate upstream PTEN, which acts to inhibit p-Akt in the inducing of a DNA damage response. However, there are many unclear points in its expression regulation and a p-Akt inhibition mechanism. For this reason, there have been reports that an expression level of PTEN increases, reports that it decreases, and reports that there is no change in the DNA damage response, and there are also reports that p-Akt is not inhibited even when an expression level of PTEN increases.

In the related art, there are no reports that an expression level of PTEN increases due to administration of a topoisomerase inhibitor of an enzyme-inhibiting type, and there are no reports that p-Akt is inhibited. Accordingly, the results of the present experimental example showing that an expression level of PTEN increases, and eventually, an expression level of p-Akt decreases or p-Akt is eliminated (after 48 hours) by 3EZ,20Ac-ingenol treatment are results that have been clarified for the first time by the inventors of the present invention. In addition, continuous activation of GSK-3β, which acts on decomposition of cyclin D1, was observed.

Experimental Example 22

(Examination of Effect of Knockdown of ATR and PTEN on Decomposition of Cyclin D1)

Whether transfer of cyclin D1 from the nucleus to the cytoplasm is ATR-dependent and PTEN-dependent was examined using siRNA against ATR and siRNA against PTEN. First, siRNA against ATR ("ON-TARGET Plus Human ATR (545) siRNA-SMARTpool," GE Dharmacon), siRNA against PTEN ("ON-TARGET Plus Human PTEN (5728) siRNA-SMARTpool," GE Dharmacon), and control siRNA ("ON-TARGET Plus Nontargeting pool," GE Dharmacon) were respectively introduced into BALL-1 cells at a final concentration of 50 nM, and incubated for 48 hours.

Subsequently, a cell medium was replaced with a new medium containing 3EZ,20Ac-ingenol at a final concentration of 0.5 µM, and culturing was performed for 24 and 48 hours. Subsequently, abundances of cyclin D1 in the nuclear fraction and the cytoplasm fraction were analyzed by Western blotting using an anti-cyclin-D1 antibody (Santa Cruz).

Figure 23:
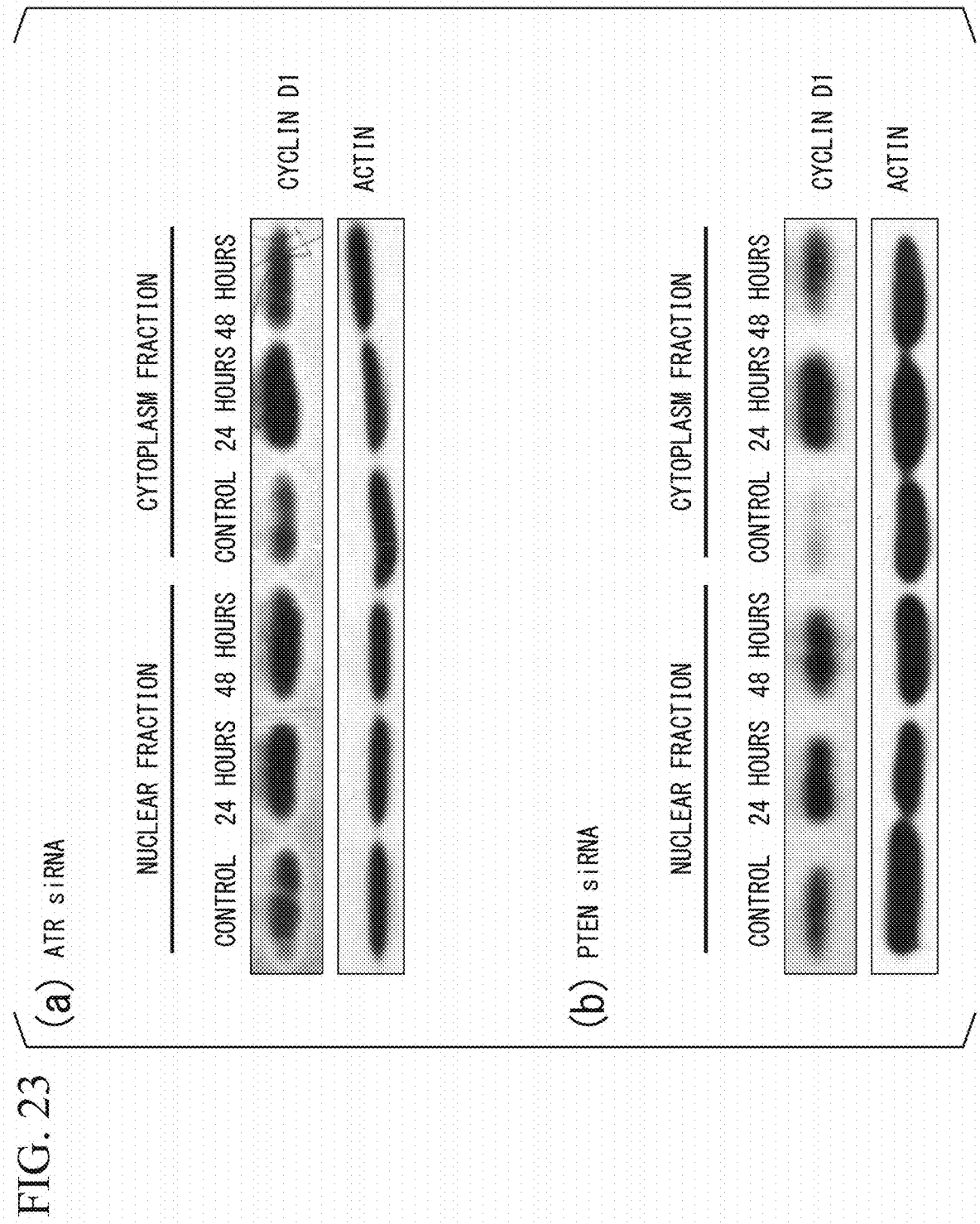
FIGS. 23(a) and 23(b) are photographs showing results of Western blotting in Experimental Example 22.

FIG. 23(a) shows results of detecting the presence of cyclin D1 by Western blotting of BALL-1 cells into which siRNA against ATR was introduced. In addition, FIG. 23(b) shows results of detecting the presence of cyclin D1 by Western blotting of BALL-1 cells into which siRNA against PTEN was introduced. Actin protein was detected as a loading control.

As a result, it became clear that an abundance of cyclin D1 was large in the nuclear fractions of the cells into which siRNA against ATR was introduced and which were then cultured for 24 and 48 hours in the presence of 3EZ,20Ac-ingenol, and the cells into which siRNA against PTEN was introduced and which were then cultured for 24 and 48 hours in the presence of 3EZ,20Ac-ingenol.

In contrast, it became clear that an abundance of cyclin D1 was small in the cytoplasm fraction of the control cells; abundances of cyclin D1 in the cytoplasm fractions increased in the cells into which siRNA against ATR was introduced and which were then cultured for 24 hours in the presence of 3EZ,20Ac-ingenol, and the cells into which siRNA against PTEN was introduced and which were then cultured for 24 hours in the presence of 3EZ,20Ac-ingenol; and abundances of cyclin D1 in the cytoplasm fractions decreased again in the cells into which siRNA against ATR was introduced and which were then cultured for 48 hours in the presence of 3EZ,20Ac-ingenol, and the cells into which siRNA against PTEN was introduced and which were then cultured for 48 hours in the presence of 3EZ,20Ac-ingenol.

Based on the above results, it became clear that when ATR or PTEN is knocked down, the transfer of cyclin D1 from the nucleus into the cytoplasm is inhibited. Accordingly, it became clear that the transfer of cyclin D1 from the nucleus into the cytoplasm is ATR-dependent and PTEN-dependent. In addition, it is thought that decomposition of cyclin D1 in the cytoplasm is not affected by ATR or PTEN.

Experimental Example 23

(Examination of Effect of Irinotecan on Proliferation of JeKo-1 Cells and Panc-1 Cells)

The effect of irinotecan, which is a topoisomerase I inhibitor of a DNA-cleavage type and is currently used clinically, on proliferation of JeKo-1 cells and Panc-1 cells was examined.

First, JeKo-1 cells were seeded in a 96-well plate at $1 \times 10^4$ cells/well/100 µL. Subsequently, irinotecan at a final concentration of 0 (control), 0.5, 1, 5, 10, 20, and 30 µM was added to the wells of the cells and culturing was performed for 48 hours. In addition, Panc-1 cells were seeded in a 96-well plate at $3 \times 10^3$ cells/well/100 µL. Subsequently, irinotecan at a final concentration of 0 (control), 0.5, 1, 5, 10, 20, 30, and 50 µM was added to the wells of the cells and culturing was performed for 48 hours. Subsequently, cell proliferation was examined by MTT assay using a Cell Proliferation Kit I (Roche Applied Science).

Figure 24:
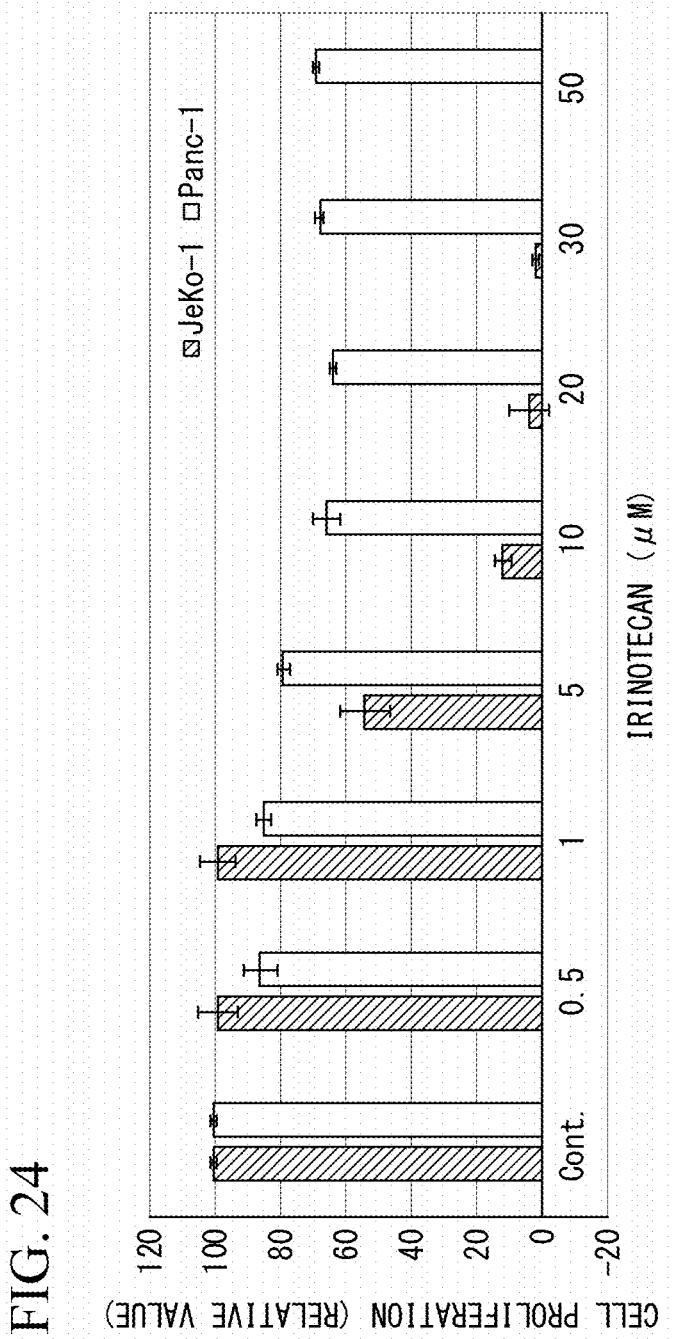
FIG. 24 is a graph showing results of MTT assay in Experimental Example 23.

FIG. 24 is a graph showing results of MTT assay. As a result, when the JeKo-1 cells were cultured in the presence of 1 to 20 µM of irinotecan, proliferation inhibition was recognized to the extent that grown cells were almost eliminated. However, the degree of proliferation inhibition was lower than in the case of 3EZ,20Ac-ingenol treatment. Meanwhile, the Panc-1 cells showed resistance in the presence of 0.5 to 50 µM of irinotecan, and complete proliferation inhibition was not confirmed. The degree of proliferation inhibition was about 30% to 35%.

Based on the results of Experimental Example 2, $IC_5O$ of 3EZ,20Ac-ingenol with respect to the JeKo-1 cells was calculated to be 0.5 µM. In addition, $IC_{50}$ of 3EZ,20Ac-ingenol with respect to the Panc-1 cells was calculated to be 3 µM. In contrast, based on the results of the present experimental example, $IC_{50}$ of irinotecan with respect to the JeKo-1 cells was calculated to be 5 µM. Furthermore, the Panc-1 cells also showed resistance to irinotecan.

The abnormal presence of cyclin D1 in cells indicates resistance to chemotherapeutic anticancer agents and anticancer effects in response to radiation therapy, and is thought to cause a poor prognosis. 3EZ,20Ac-ingenol specifically acted on cancers having such properties, and was able to reduce an abundance of cyclin D1 or eliminate cyclin D1 which is the cause thereof. This suggests that the Panc-1 cells also induced proliferation inhibition and apoptosis without showing resistance to 3EZ,20Ac-ingenol treatment.

In addition, it is reported that the abnormal presence of cyclin D1 in the cytoplasm is related to invasion and metastasis of cancer. Due to 3EZ,20Ac-ingenol treatment, in the cytoplasms of both JeKo-1 cells and Panc-1 cells, an increase in PTEN level was confirmed, and a decrease in abundance of cyclin D1 could be observed.

Irinotecan is a kind of prodrug and functions by being converted into an active metabolite SN-38 by liver carboxylesterase or the like. Although the activity of carboxylesterase differs between individuals, 3EZ,20Ac-ingenol is not metabolically activated and thus is considered to be clinically useful.

Experimental Example 24

(Examination of Compounds Similar to 3EZ,20Ac-Ingenol)

BALL-1 cells were exposed to 3EZ,20Ac-ingenol, 3EE, 20Ac-ingenol, 20Ac-ingenol, and ingenol at concentrations of 0.01, 0.05, 0.1, 0.5, and 1 µM for 48 hours. Thereafter, cell proliferation was examined by MTT assay. Cells that were not exposed to the chemical were used as controls. The chemical formulas of 3EZ,20Ac-ingenol, 3EE,20Ac-ingenol, and 20Ac-ingenol are as described above. The chemical formula of ingenol is shown in the following Formula (7).

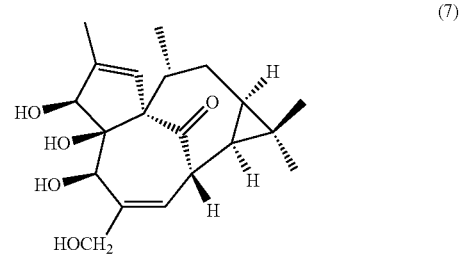

(7)

Figure 25:
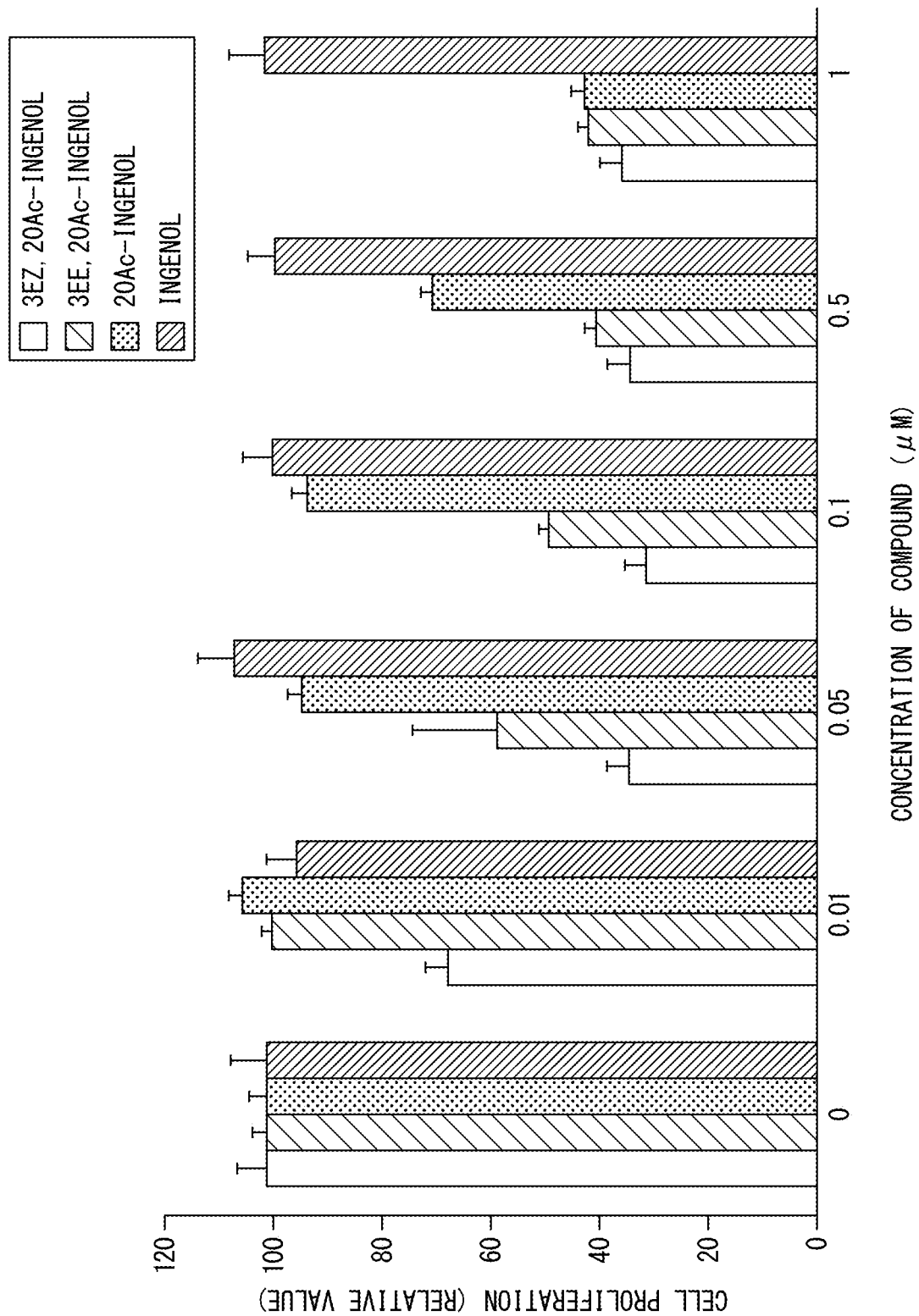
FIG. 25 is a graph showing results of MTT assay in Experimental Example 24.

FIG. 25 is a graph showing results. As a result, a significant level of inhibition of proliferation of the BALL-1 cells was observed in the presence of 3EZ,20Ac-ingenol and 3EE,20Ac-ingenol. In addition, inhibition of proliferation of the BALL-1 cells was observed even in the presence of 20Ac-ingenol. On the other hand, ingenol had little effect on proliferation of the BALL-1 cells.

INDUSTRIAL APPLICABILITY

According to the present invention, it is possible to provide an anticancer agent that specifically acts on a specific cancer without causing DNA cleavage.

The invention claimed is:

1. A method for treating cancer, comprising:
measuring an abundance of cyclin D1 protein in cancer cells derived from a cancer patient, and
administering an effective amount of a compound represented by the following Formula (1) (in Formula (1), $R^1$ to $R^{11}$ each independently represent a hydrogen atom, an aliphatic group having 1 to 30 carbon atoms, or a group represented by Formula RCO-(where, R represents an aliphatic group having 1 to 30 carbon atoms, or an aromatic group or heteroaromatic group having 1 to 10 carbon atoms)) to the cancer patient in case where the measured abundance of cyclin D1 protein is greater than that in a control

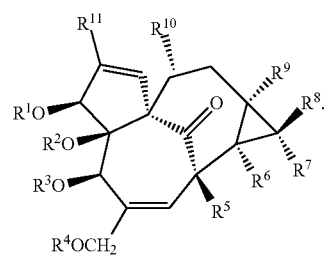
(1)

2. A method for treating cancer, comprising:
culturing cancer cells derived from a cancer patient in the presence of the compound represented by the following Formula (1) (in Formula (1), $R^1$ to $R^{11}$ each independently represent a hydrogen atom, an aliphatic group having 1 to 30 carbon atoms, or a group represented by Formula RCO-(where, R represents an aliphatic group having 1 to 30 carbon atoms, or an aromatic group or heteroaromatic group having 1 to 10 carbon atoms)),
measuring transfer of cyclin D1 protein from a nucleus into a cytoplasm of the cell, and
administering an effective amount of the compound represented by the following Formula (1) to the cancer patient in case where the cyclin D1 protein in the cytoplasm of the cancer cells after the culturing in the presence of the compound represented by the following Formula (1) for 12 to 24 hours was increased when compared to the cyclin D1 protein in the cytoplasm of the cancer cells culturing in the absence of the compound represented by the following Formula (1)

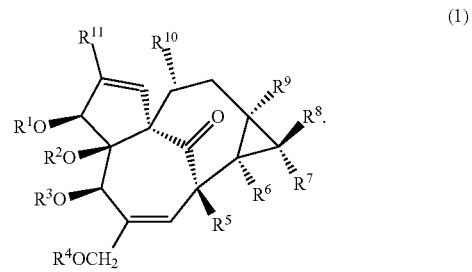
(1)

3. A method for treating cancer, comprising:
culturing cancer cells derived from a cancer patient in the presence of the compound represented by the following Formula (1) (in Formula (1), $R^1$ to $R^{11}$ each independently represent a hydrogen atom, an aliphatic group having 1 to 30 carbon atoms, or a group represented by Formula RCO-(where, R represents an aliphatic group having 1 to 30 carbon atoms, or an aromatic group or heteroaromatic group having 1 to 10 carbon atoms)),
measuring an abundance of cyclin D1 protein in a nucleus of the cell, and
administering an effective amount of the compound represented by the following Formula (1) to the cancer patient in case where the cyclin D1 protein in the nucleus of the cancer cells after the culturing in the presence of the compound represented by the following Formula (1) for 12 to 24 hours was decreased when compared to the cyclin D1 protein in the nucleus of the cancer cells culturing in the absence of the compound represented by the following Formula (1)

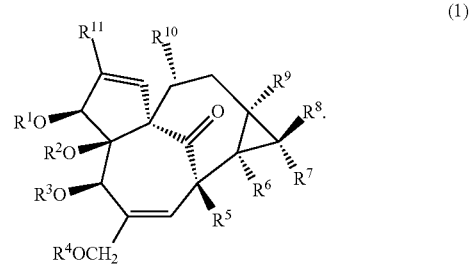
(1)

4. The method for treating cancer according to claim 2, wherein an effective amount of the compound represented by the Formula (1) is administered to the cancer patient in the administering in case where the cyclin D1 protein in the cytoplasm of the cancer cells after the culturing in the presence of the compound represented by the Formula (1) for 48 hours was decreased when compared to the cyclin D1 protein in the cytoplasm of the cancer cells after the culturing in the presence of the compound represented by the Formula (1) for 12 to 24 hours.

5. The method for treating cancer according to claim 3, wherein an effective amount of the compound represented by the Formula (1) is administered to the cancer patient in the administering in case where the cyclin D1 protein in the nucleus of the cancer cells after the culturing in the presence of the compound represented by the Formula (1) for 48 hours was further decreased when compared with the cyclin D1 protein in the nucleus of the cancer cells after the culturing in the presence of the compound represented by the Formula (1) for 12 to 24 hours.

* * * * *